United States Patent [19]

Russell et al.

[11] Patent Number: 5,527,884
[45] Date of Patent: Jun. 18, 1996

[54] MEDIATORS OF CHRONIC ALLOGRAFT REJECTION AND DNA MOLECULES ENCODING THEM

[75] Inventors: Mary E. Russell, Carlisle; Ulrike Utans, Cambridge, both of Mass.

[73] Assignee: President and Fellows of Harvard College, Cambridge, Mass.

[21] Appl. No.: 171,385

[22] Filed: Dec. 21, 1993

[51] Int. Cl.$^6$ .......................... C12N 15/12; C07K 14/435
[52] U.S. Cl. ............................................. 530/350; 536/23.5
[58] Field of Search .............................. 536/24.33, 24.5, 536/24.3, 24.31, 23.5, 23.53; 530/350, 387.1; 435/6, 69.1; 514/2, 12

[56] References Cited

PUBLICATIONS

Papp et al., "Evidence for Functional Heterogeneity of Rat CD4+ T Cells in vivo", 1992, J. Immunology, 148(5):1308–14.

Utans et al., "Chronic Cardiac Rejection: Identification of Five Upregulated Genes in Transplanted Hearts by Differential mRNA Display", 1994, Proc. Natl. Acad. Sciences, 91:6463–67.

Sharples, L. D., et al., "Risks Factor Analysis For The Major Hazards Following Heart Transplantation–Rejection, Infection, and Coronary Occulusive Disease", 1991, Transplantation, vol. 52, No. 2, pp. 244–252.

Cramer, D. V., et al., "Lymphocytic Subsets and Histopathologic Changes Associated with the Development of Heart Transplant Arteriosclerosis", 1992, J. Heart Lung Transplant., vol. 11, No. 3, pp. 458–466.

Adams, D. H., et al., "Experimental Graft Arteriosclerosis", 1992, Transplantation, vol. 53, No. 5, pp. 1115–1119.

Adams, D. H., et al., "Experimental Graft Arteriosclerosis", 1993, Transplantation, vol. 56, No. 4, pp. 794–799.

Russell, M. E., et al., "Early and Persistent Induction of Monocyte Chemoattractant Protein 1 in Rat Cardiac Allografts", 1993, Proc. Natl. Acad. Sci. USA, vol. 90, pp. 6086–6090.

Liang, P., et al., "Differential Display of Eukaryotic Messenger RNA by Means of the Polymerase Chain Reaction", 1992, Science, vol. 257, pp. 967–971.

Steinbeck, M. J., et al., "Intracellular Production of Singlet Oxygen by Simulated Macrophages Quantified Using 9,10–Diphenylanthracene and Perylene in a Polystyrene Film", 1993, J. Biologic. Chem., vol. 268, No. 21, pp. 15649–15654.

Arceci, R., et al., "Mouse GATA–4: a Retinoic Acid–Inducible GATA–Binding Transcription Factor Expressed in Endodermally Derived Tissues and Heart", 1993, Mol. and Cell. Biol., vol. 13, No. 4, pp. 2235–2246.

Ii, M., et al., "Molecular Cloning and Sequence Analysis of cDNA Encoding the Macrophage Lectin Specific for Galactose and N–Acetylgalactosamine", 1990, J. Biol. Chem., vol. 265, No. 19, pp. 11295–11298.

Oda, S., et al., "Purification and Characterization of a Lectin–Like Molecule Specific for Galactose/N–Acetyl–Galactosamine from Tumoricidal Macrophages", 1988, J. Biochem., vol. 104, pp. 600–605.

Oda, S., et al., "Binding of Activated Macrophages to Tumor Cells Through a Macrophage Lectin and Its Role in Macrophage Tumoricidal Activity", 1989, J. Biochem., vol. 105, pp. 1040–1043.

Sharon, N., et al., "Lectins as Cell Recognition Molecules", 1989, Science, vol. 246, pp. 227–234.

Kawasaki, T., et al., "Isolation and Characterization of a Receptor Lectin Specific for Galactose/N–Acetylgalactosamine From Macrophages", 1986, Carbohydr. Res., vol. 151, pp. 197–206.

Ii, M., et al., "Structural Similarity Between the Macrophage Lectin Specific For Galactose/N–Acetylgalactosamine and the Hepatic Asialogylcoprotein Binding Protein", 1988, Biochem. Biophys. Res. Commun., vol 155, No. 2, pp. 720–725.

Ozaki, K., et al., "Expression of a Funcitonal Asialoglycoprotein Receptor Through Transfection of a Cloned cDNA That Encodes a Macrophage Lectin", 1992, J. Biologic. Chem., vol. 267, No. 13, pp. 9229–9235.

Valente, A. J., et al., "Mechanisms in Intimal Monocyte–Macrophage Recuitment: A Special Role for Monocyte Chemotactic Protein–1", 1992, Supplement III, Circulation, vol. 86, No. 6, pp. III–20–III–25.

Auger, M. J., et al., In the Macrophage, C. E. Lewis and J. O'D. McGee, "Macrophage Surface Receptors", 1992, IRL Press, Oxford, Ch. 8, pp. 16–25.

Welsh, J., et al., "Arbitrarily Primed PCR Fingerprinting of RNA", 1992, Nucl. Acids Res., vol. 20, No. 19, pp. 4965–4970.

Fyfe, A., et al., "Coronary Sinus Sampling of Cytokines After Heart Transplantation: Evidence for Macrophage Activaiton and Interleukin–4 Production Within the Graft", 1993, J. Am. Cardiol., vol. 21, No. 1, pp. 171–176.

Laborda, J., "36B4 cDNA Used as an Estradiol–Independent mRNA Control is the cDNA for Human Acidic Ribosomal Phosphoprotein PO", 1991, Nucl. Acids Res., vol. 19, No. 14, pp. 3998.

Liang, P., et al., "Distribution and Cloning of Eukaryotic mRNAs by Means of Differential Display: Refinements and Optimization", 1993, Nucl. Acids Res., vol. 21, No. 14, pp. 3269–3275.

Kumar, S. et al., "Identification of a Set of Genes With Developmentally Down–Regulated Expression in the Mouse Brain", 1992, Biochem. Biophys. Res. Commun., vol. 185, No. 3, pp. 1155–1161.

(List continued on next page.)

Primary Examiner—Marianne P. Allen
Attorney, Agent, or Firm—Fish & Richardson

[57] ABSTRACT

Differentially expressed allograft genes, methods of screening therefor, and methods of diagnosing and treating allograft rejection.

3 Claims, 9 Drawing Sheets

OTHER PUBLICATIONS

Thommes, P., et al., "Properties of the Nuclear P1 Protein, a Mammalian Homologue of the Yeast Mcm3 Replication Protein", 1992, *Nucl. Acids. Res.*, vol. 20, No. 5, pp. 1069–1074.

Liang, P., et al., "Differential Display and Cloning of Messenger RNAs from Human Breast Cancer versus Mammary Epithelial Cells", 1992, vol. 52, pp. 6966–6968.

Sager, R., et al., "Identification by Differential Display of Alpha 6 Integrin as a Candidate Tumor Suppressor Gene", 1993, *FASEB J.*, vol. 7, No. 10, pp. 964–970.

Liaw, L., et al., "of Gene Expression in Bovine Aortic In Vivo Versus In Vitro: Differences in Growth Regulatory Molecules", 1993, *Arterioscler. Thromb.*, vol. 13, No. 7, pp. 985–993.

Hershko, A., et al., "The Ubiquitin System for Protein Degradation", 1992, *Annu. Rev. Biochem.*, vol. 61 pp. 761–807.

Mayer, R. J., et al., "Ubiquitin in Health and Disease", 1991, *Biochimica et Biophys. Acta.*, vol. 1089, pp. 141–157.

Iris, F. J. M., et al., "Dense Alu Clustering and a Potential New Member of the NFκB Family Within a 90 Kilobase HLA Class III Segment", 1993, *Nature Genetics*, vol. 3, pp. 137–145.

Sargent, C. A., et al., "Identification of Multiple HTF–Island Associated Genes in the Human Major Histocompatibility Complex Class III Region", 1989, *EMBO J.*, vol. 8, No. 8, pp. 2305–2312.

Stamper, H. B., et al., "An In Vitro Model of Lymphocyte Homing, I. Characterization of the Interaction between Thoracic Duct Lymphocytes and Specialized High–Endothelial Venules of Lymph Nodes", 1977, *J. Immunol.*, vol. 119, No. 2, pp. 772–780.

Butcher, E. C., et al., "Lymphocyte Adherence to High Endothelial Venules: Characterization of a Modified In Vitro Assay, and Examination of the Binding of Syngeneic and Allogeneic Lymphocyte Populations", 1979, *J. Immunol.*, vol. 123, No. 5, pp. 1996–2003.

Gessl, A., et al., "Expression of a Binding Structure for Sailic Acid Containing Glycoconjugates on Rat Bone Marrow–Derives Macrophages and its Modulation by IFN, TNF–α, and Dexamethasone", 1989, *J. Immunol.*, vol. 142, No. 12, pp. 4372–4377.

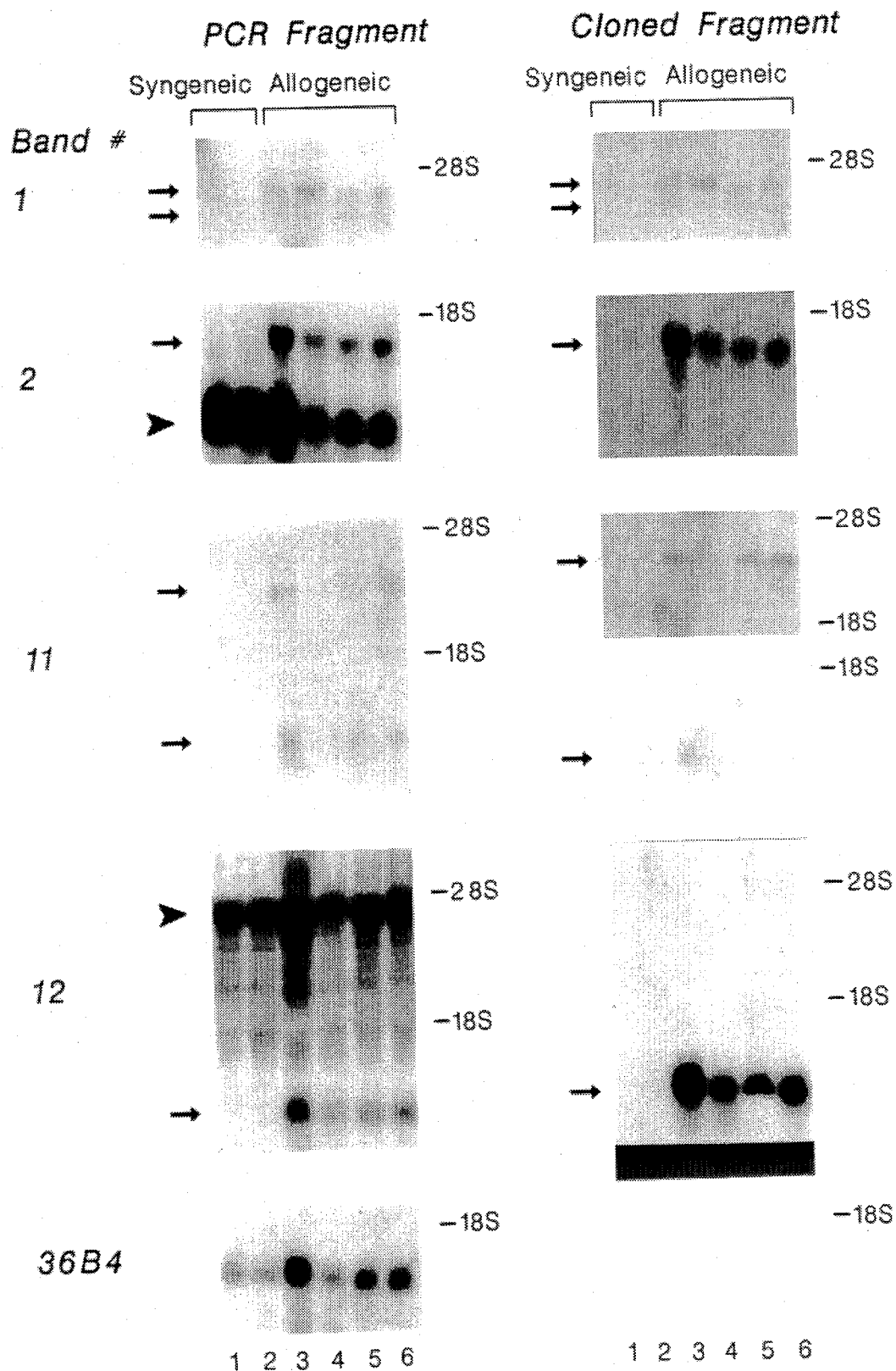

MEDIATORS OF CHRONIC ALLOGRAFT REJECTION AND DNA MOLECULES ENCODING THEM

STATEMENT AS TO FEDERALLY SPONSORED RESEARCH

This invention was made with U.S. Government support under HL43318 awarded by the National Institutes of Health. The U.S. Government therefore has certain rights in the invention.

BACKGROUND OF THE INVENTION

The invention relates to tissue and organ transplantation.

The major limitation to long-term survival after organ transplantation in humans is the development of chronic rejection. Cardiac transplantation, for example, is frequently characterized by an obliterative arteriosclerosis with progressive thickening of the interior of the blood vessel that eventually results in ischemic injury (Schoen, F. J. and P. Libby, 1991, Cardiac Transplant Graft Arteriosclerosis, *Trends Cardiovasc. Med.*, 1:216–223; Sharples, L. D., N. Caine, P. Mullins, J. P. Scott, E. Solis, T. A. English, S. R. Large, P. M. Schofield, and J. Wallwork, 1991, Risk factor analysis for the major hazards following heart transplantation-rejection, infection, and coronary occlusive disease, *Transplantation*, 52:244–252; Cramer, D. V., 1993, Graft Arteriosclerosis in Heart Transplantation, R. G. Landes Company, Austin, Tex.). Studies of vessels from human heart transplant recipients have revealed an intimal hyperplasia that is concentric and diffuse, involves a spectrum of vessels, and is highly prevalent. In the first stage of arteriosclerotic thickening, monocytes/macrophages accumulate. In the intermediate stage, macrophages and smooth muscle cells both accumulate, and in the later more obliterative stage, smooth muscle cells predominate.

Chronic transplant rejection is likely to be a complex process mediated by a spectrum of factors which have been difficult to eliminate. Transplant arteriosclerosis occurs only in the donor heart and spares the host vessels. One hypothesis about the arteriosclerotic process holds that a chronic, cell-mediated immune response to alloantigens produces cytokines that mediate neointimal smooth muscle cell accumulation in the graft-derived vasculature, in a manner analogous to the process of delayed-type hypersensitivity (Schoen et al., supra), but little is known about factors that regulate the specific localization or function of mononuclear cells in the interstitium and vessels of cardiac allografts. The pathogenesis of transplant arteriosclerosis is unknown, and studies to elucidate the process have been limited by difficulty in obtaining useful clinical specimens.

SUMMARY OF THE INVENTION

The invention addresses these problems by providing methods to identify genes which are differentially expressed in allograft tissue undergoing rejection, to diagnose chronic rejection, and to treat patients undergoing transplant rejection.

As an alternative to conventional transcriptional analysis of selected known factors that could be involved in chronic rejection, screening assays which utilize a modification of the differential mRNA display technique were developed to identify potential mediators that are novel or have not been previously implicated in chronic rejection.

In one aspect, the invention features a method of identifying a gene which is differentially expressed in an allograft of a given tissue type compared to a syngraft of the same tissue type, by obtaining mRNA from the allograft and syngraft and determining whether the amount per cell of an allograft transcript is increased or decreased compared to that of the corresponding syngraft transcript. An increase in the amount of a given transcript in tissue from an allograft compared to the amount of the corresponding transcript in corresponding tissue from a syngraft indicates that the given transcript encodes a mediator of allograft rejection. The term "differentially expressed" refers to a given allograft gene transcript, and is defined as an amount which is substantially greater or less than the amount of the corresponding syngraft transcript. By the term "gene transcript" is meant a mRNA or cDNA.

In one embodiment, the amount of allograft transcript is at least four times the amount of the corresponding syngraft transcript; preferably, the amount of syngraft transcript is absent or undetectable.

In another aspect, the invention features a method of diagnosing allograft rejection in a patient by detecting a differentially expressed allograft gene or polypeptide product thereof. Detection of genes previously identified using the screening assays of the invention, such as allograft inflammatory factor-1 (AIF-1), allograft inflammatory factor-2 (AIF-2), ubiquitin, P1 or galactose/N-acetylgalactosamine (Gal/GalNAc) macrophage lectin, can be used to diagnose transplant rejection in a patient. Detection of differentially expressed genes can be accomplished by measuring gene transcripts, e.g., mRNA or cDNA, using standard techniques such as differential display mRNA analysis, polymerase chain reaction (PCR), in situ hybridization, or Northern blotting techniques, or by measuring the polypeptide product using known methods, such as Western blotting techniques or fluorescein-activated cell sorting (FACS).

The invention also features an isolated DNA which contains the sequence of SEQ ID NO:4 encoding AIF-1. An isolated DNA which hybridizes at high stringency to a 20 nucleotide fragment of SEQ ID NO: 1 or 4, and an isolated DNA which encodes a protein containing the amino acid sequence of SEQ ID NO: 5, are also included. A substantially pure preparation of a polypeptide containing the sequence of SEQ ID NO:5 is also included. The DNA of the invention preferably encodes a mammalian AIF-1 polypeptide or functional fragment or isoform thereof, and most preferably encodes a rat or a human AIF-1 polypeptide.

An isolated DNA which includes the sequence of SEQ ID NO: 2, 3, 8, 9, 10, 11, 12, 13, 14, 15, 16, 17, 18, 19, 20, 21, 22, 23, 24, 25, 26, or 27 is also within the invention, as well as an isolated DNA which hybridizes at high stringency to a DNA containing such a sequence. A substantially pure preparation of a polypeptide containing sequences encoded by the DNA of SEQ ID NO: 2, 3, 8, 9, 10, 11, 12, 13, 14, 15, 16, 17, 18, 19, 20, 21, 22, 23, 24, 25, 26, or 27 is also within the invention. The DNA of the invention preferably encodes a mammalian AIF-2 polypeptide or functional fragment or isoform thereof, and most preferably encodes a rat or a human AIF-2 polypeptide. The invention encompasses isolated DNA containing part or all of the sequence of either AIF-1 or AIF-2. Also included are vectors containing the isolated DNA; cells, which can be prokaryotic or eukaryotic, containing the isolated DNA; and methods of manufacturing recombinant AIF-1 or AIF-2, such as methods culturing the cells containing isolated DNA of the invention under conditions permitting expression of the DNA. An "isolated DNA", as used herein, refers to a given DNA sequence which may be single stranded or double stranded, sense or antisense and which has been removed from the sequences which flank it in a naturally occurring state, e.g., the sequences adjacent to the given DNA sequence in a genome in which it naturally occurs. The term includes, for example, a recombinant DNA which is incorporated into a vector, into an autonomously replicating plasmid or virus, or into the genomic DNA of a prokaryote or eukaryote; or which exists as a separate molecule (e.g., a cDNA or a genomic DNA fragment produced by PCR or restriction endonuclease treatment) independent of other DNA sequences. The term "substantially pure" describes a compound, e.g., a polypeptide, which has been separated from components which naturally accompany it. Typically, a polypeptide is substantially pure when at least 10%, more preferably at least 20%, more preferably at least 50%, more preferably at least 75%, more preferably at least 90%, and most preferably at least 99% of the total material by dry weight in a sample is the polypeptide of interest. Purity can be measured by any appropriate method, e.g., polyacrylamide gel electrophoresis, column chromatography, or HPLC analysis. By the term "high stringency" is meant DNA hybridization and wash conditions characterized by relatively high temperature and low salt concentration, e.g., conditions described in Sambrook et al., 1989, *Molecular Cloning: a Laboratory Manual*, second edition, Cold Spring Harbor Press, Cold Spring Harbor, N.Y., e.g., 0.2×SSC, 0.1% SDS at 60° C. wash conditions.

In another aspect, the invention features a method of inhibiting rejection of a transplanted tissue in an animal, by introducing into the animal a compound which inhibits expression of a differentially expressed allograft transcript that is upregulated during rejection of an allograft. An example of such a compound is an antisense DNA fragment complementary to the coding sequence of a differentially expressed allograft gene, e.g., Gal/GalNAc macrophage lectin, AIF-1, AIF-2, ubiquitin, or P1.

The invention also features a method of inhibiting rejection of a transplanted tissue in an animal by introducing into the animal a compound which inhibits binding of a cell-associated lectin to a carbohydrate ligand on the allograft. In preferred embodiments, the lectin is Gal/GalNAc macrophage lectin, and/or is present on the surface of a macrophage. The invention also includes compounds which inhibit binding of the lectin to its carbohydrate ligand, such as Gal/GalNAc macrophage lectin-specific antibody, a polypeptide which binds to Gal/GalNAc, a carbohydrate or compound containing a carbohydrate which binds to Gal/GalNAc macrophage lectin, or a compound containing a soluble carbohydrate-binding fragment of Gal/GalNAc macrophage lectin, all of which may be formulated in a pharmaceutical excipient for administration to animals.

In another aspect, the invention includes a screening assay to identify a candidate compound capable of inhibiting allograft rejection, by contacting Gal/GalNAc macrophage lectin with its carbohydrate ligand in the presence and absence of a candidate compound, and measuring binding of the lectin to its carbohydrate ligand. A decrease in binding in the presence of a candidate compound compared to the level of binding in the absence of the candidate compound is an indication that the candidate compound inhibits allograft rejection. This screening method may be carried out in vitro as well as in vivo.

Other features and advantages of the invention will be apparent from the following detailed description and other embodiments of the invention, and from the claims.

$^{32}$P incorporation in the PCR product band from dried gels was measured in PhosphorImager units. The linear relationship between amplified Gal/GalNAc macrophage lectin product bands and PCR cycle identifies the assay range where amplified product is proportional to the initial target mRNA.

Figure 4A:
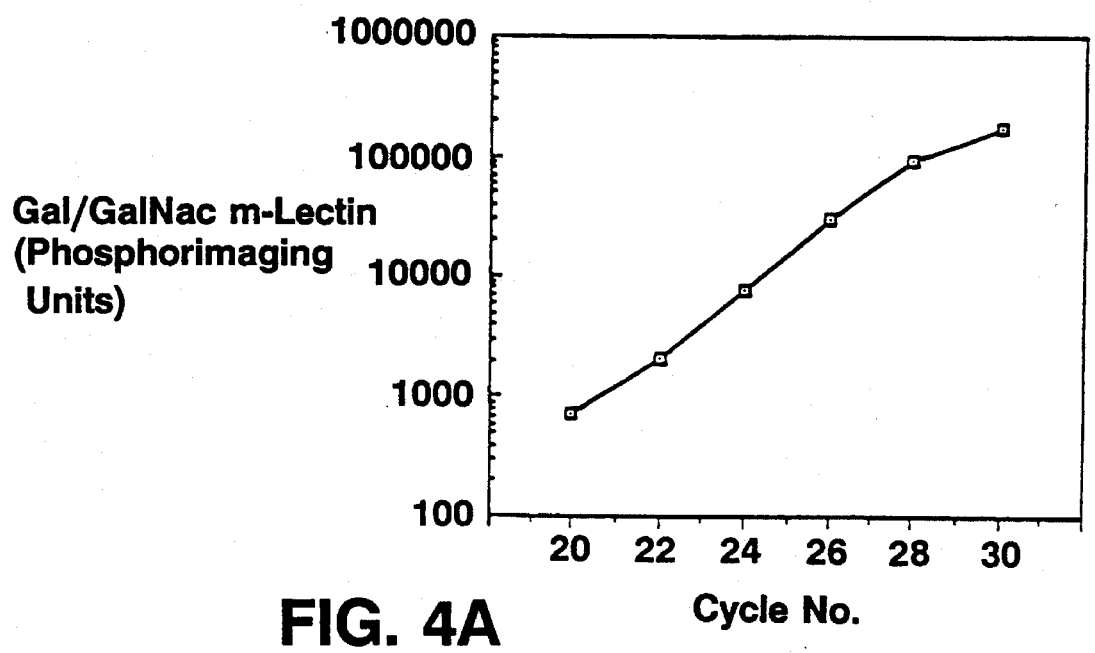
FIG. 4A is a graph of the linear range of Gal/GalNAc macrophage lectin reverse transcription-PCR assay. Rat cardiac allograft cDNA was amplified using specific Gal/GalNAc macrophage lectin primers and separated electrophoretically on 1% agarose gels.
Figure 4B:
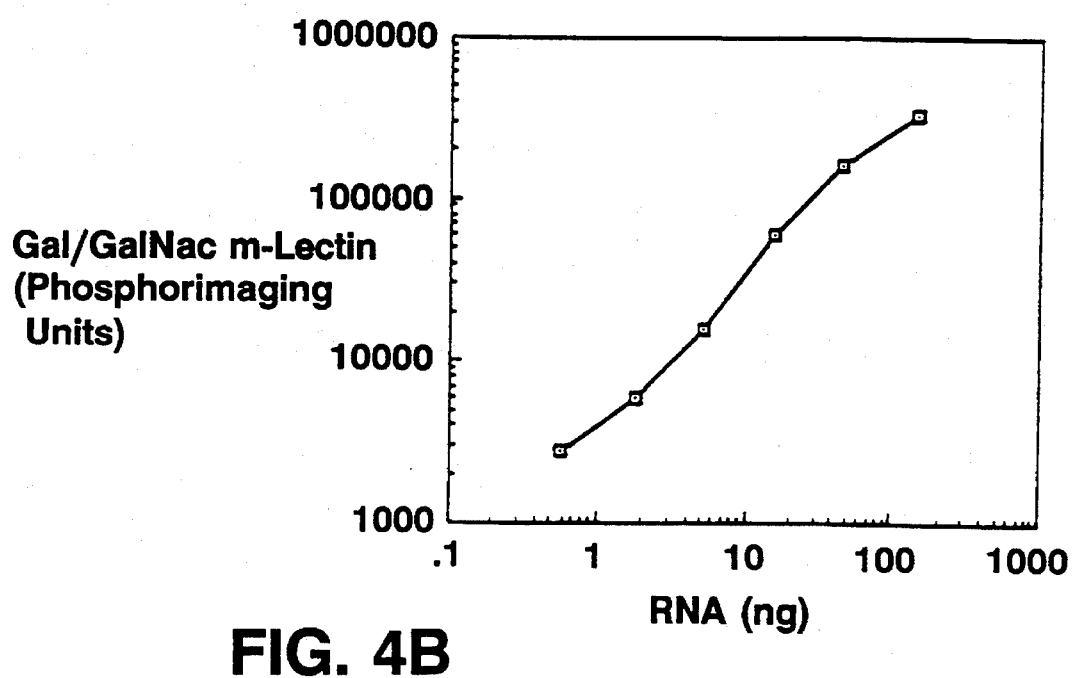

FIG. 4B is a graph showing the linear relationship between amplified Gal/GalNAc macrophage lectin product bands and added cDNA (represented as the calculated amount of total RNA in the PCR reaction, lower panel) which identifies the assay range where amplified product is proportional to the initial target mRNA.

Figure 5:
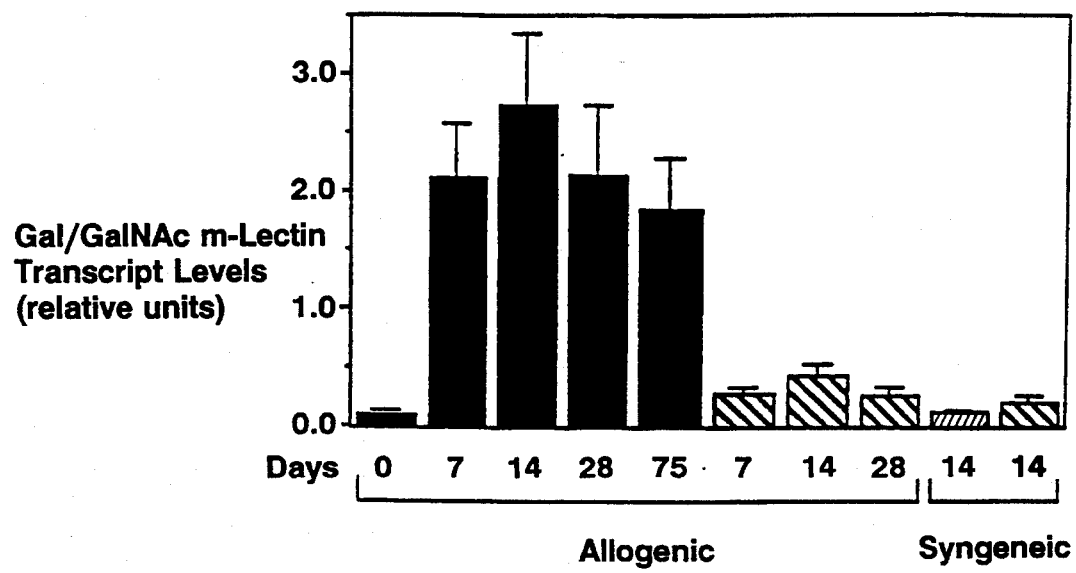

FIG. 5 is a bar graph showing a time course of Gal/GalNAc macrophage lectin gene expression after allogeneic cardiac transplantation. Corrected levels were derived by normalizing Gal/GalNAc macrophage lectin PCR values against those for the control gene, Glyceraldehyde 3 phosphate dehydrogenase (G3PDH), and are shown in relative units. There was a significant increase in cardiac transplant (or allograft) cDNA at 7, 14, 28, and 75 days (black bars) following transplantation compared with cDNA from the day-0 heart (harvested but not transplanted), paired host hearts (hatched bars), and a 14-day syngraft (stippled bar) ($P<0.008$). Data are plotted as means ±SEM and represent 4 separate PCR analyses.

Figure 6:
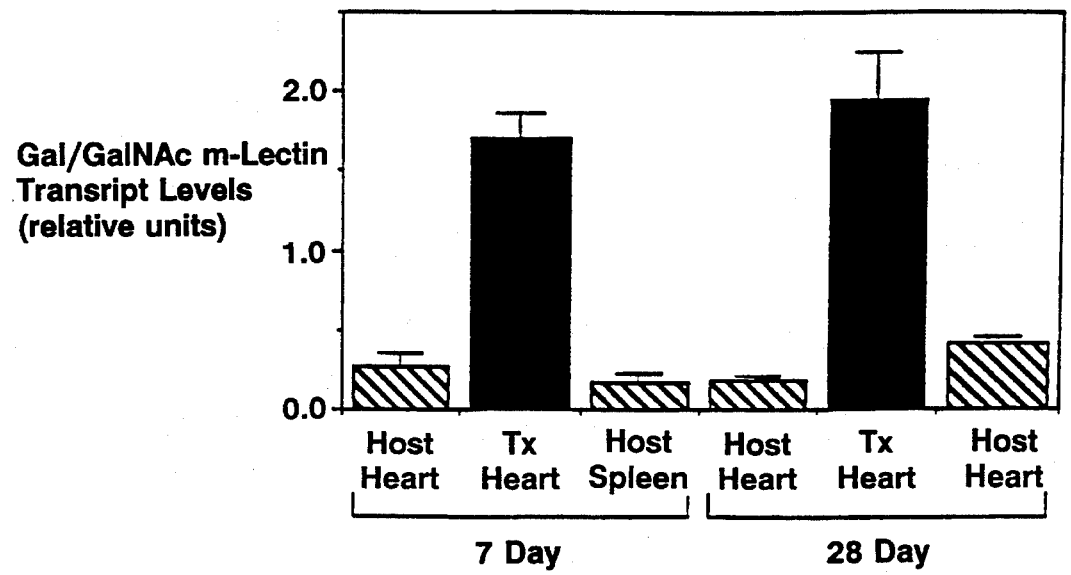

FIG. 6 is a bar graph showing upregulation of Gal/GalNAc macrophage lectin transcripts localized within the allografted heart. PCR analysis to identify relative differences in Gal/GalNAc macrophage lectin transcript levels was performed on a set of cDNAs that included the transplanted heart (black bars) and the matching host heart and spleen (hatched bars) from 2 additional allogeneic cardiac transplantations harvested at 7 and 14 days. Corrected Gal/GalNAc macrophage lectin levels were derived by normalizing the lectin PCR band value against that of the G3PDH control value. Gal/GalNAc macrophage lectin levels increased significantly in the transplanted hearts compared with the host spleens (rich in resident macrophages but not subject to local allogeneic stimulation) and the host hearts normal on histologic examination ($P<0.0001$). Data are plotted as means ±SEM and represent 4 separate PCR analyses.

Figure 7:
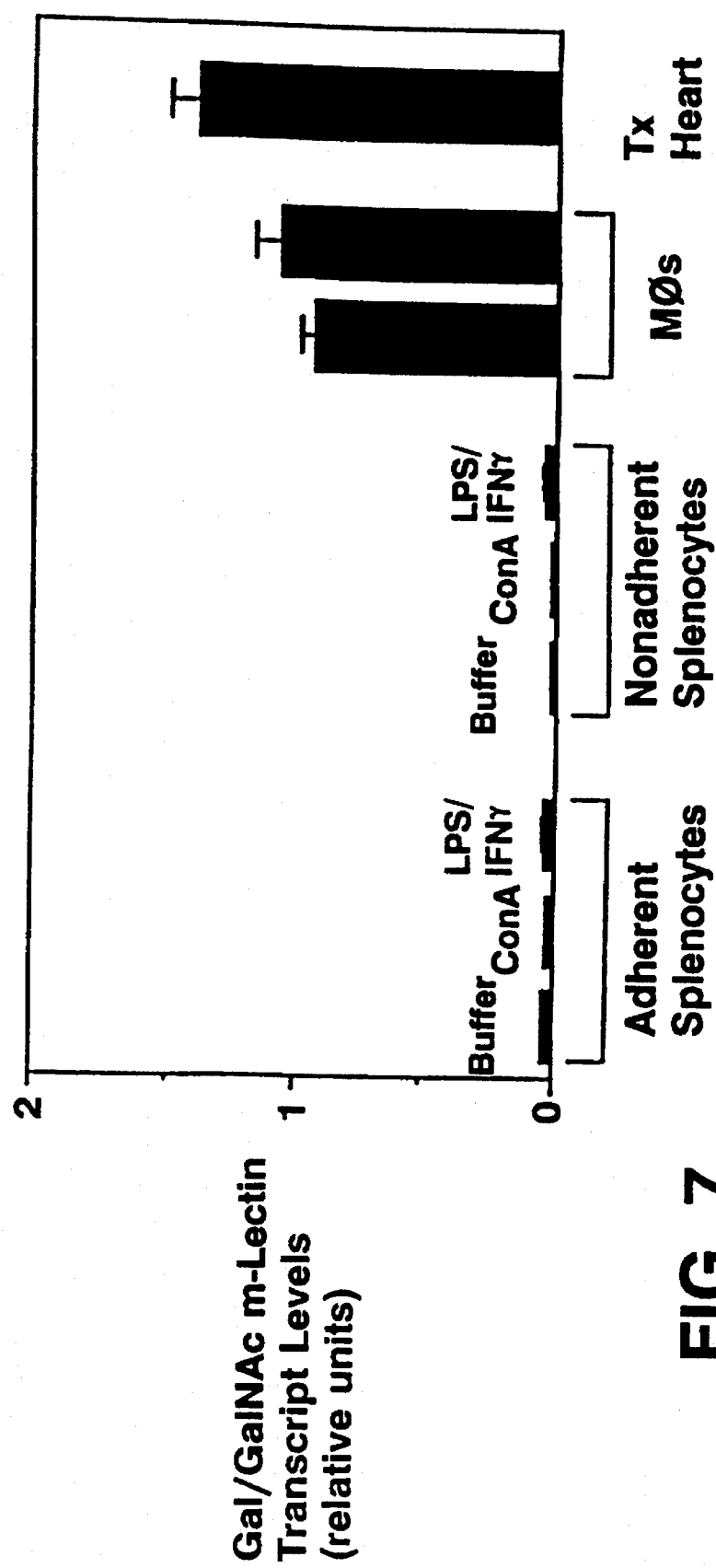

FIG. 7 is a bar graph showing an increase in Gal/GalNAc transcripts levels in exudative macrophages. Corrected Gal/GalNAc transcript levels were significantly higher in thioglycolate-elicited macrophages ($P<0.0001$) and cardiac allografts compared with adherent and nonadherent splenocytes even after 4 hours of stimulation with concanavalin A or lipopolysaccharide/interferon-γ. Data are plotted as means ±SEM and represent 4 separate PCR analyses.

Figures 8A, 8B, 8C, 8D:
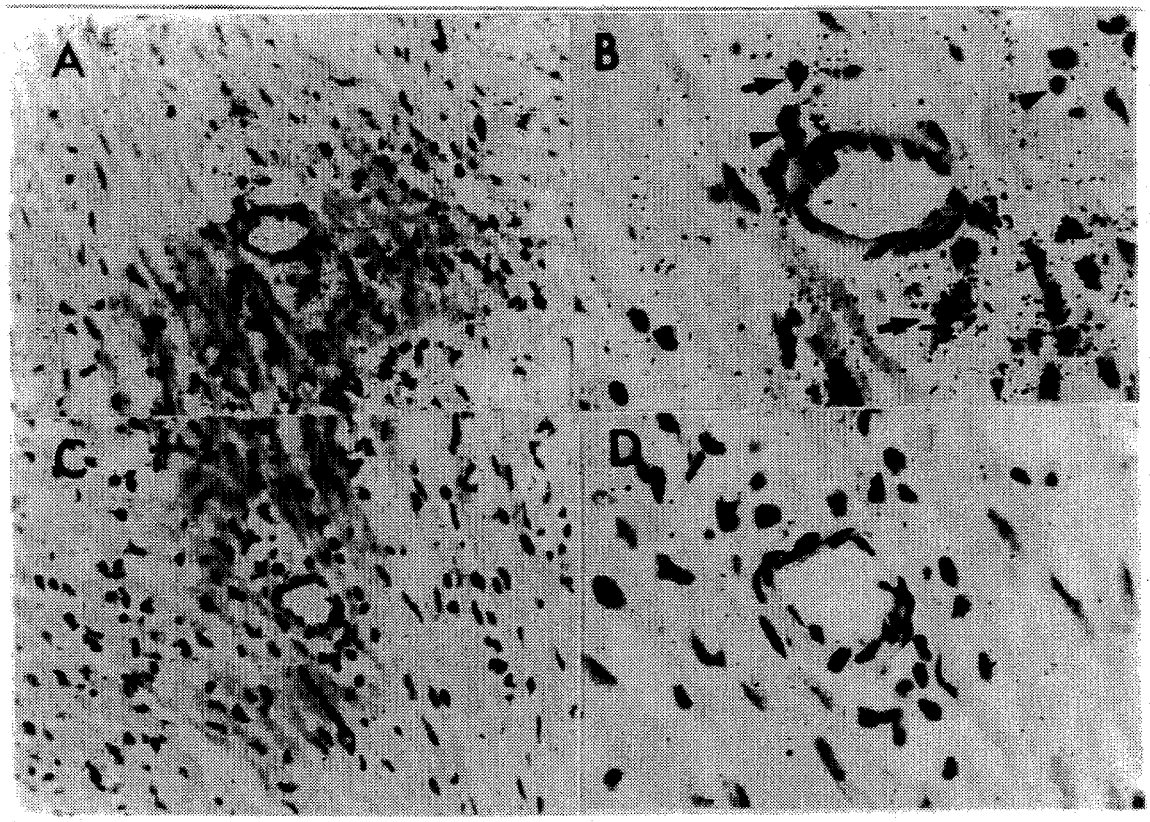

FIGS. 8A–8D are photographs of microscopic analyses of cardiac allograft cells showing in situ localization of Gal/GalNAc macrophage lectin mRNA. Sections were hybridized to $^{35}$S-labeled antisense (FIG. 8A and FIG. 8B) or sense (FIG. 8C and FIG. 8D) riboprobes. Arrows in lower-power sections (FIG. 8A and FIG. 8C) indicate the regions shown in higher magnification (FIG. 8B and FIG. 8D). Silver grains indicating hybridization of Gal/GalNAc macrophage lectin mRNA are clustered over a subset of inflammatory cells in the interstitium and perivascular spaces (FIG. 8A, 260×). Arrows mark representative positive mononuclear cells that are seen best at higher magnification (FIG. 8B, 600×). Arrowheads mark representative inflammatory cells without hybridization. Little hybridization is visible in adjacent noninflammatory cells such as cardiac myocytes. The sections hybridized with sense riboprobes show no significant hybridization (FIG. 8C, 260×) and (FIG. 8D, 600×).

Figure 9A:
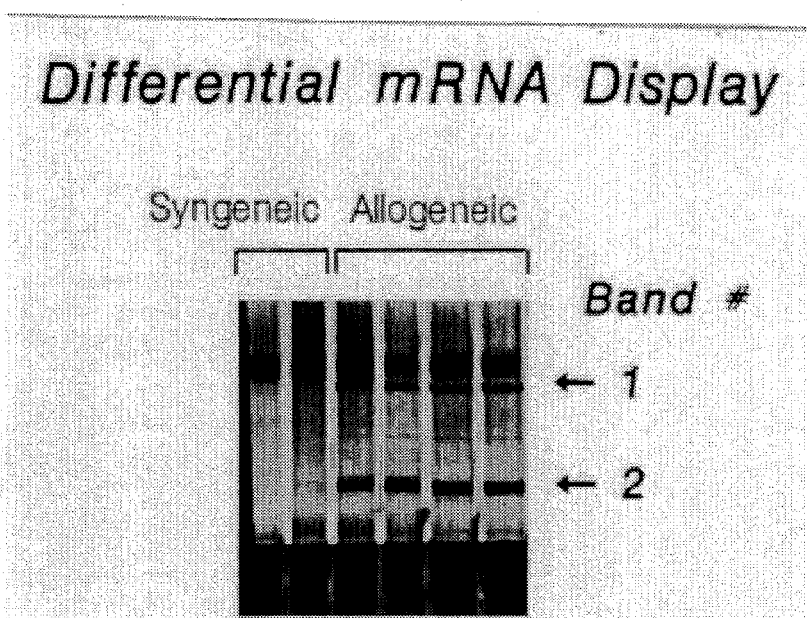
Figure 9B:
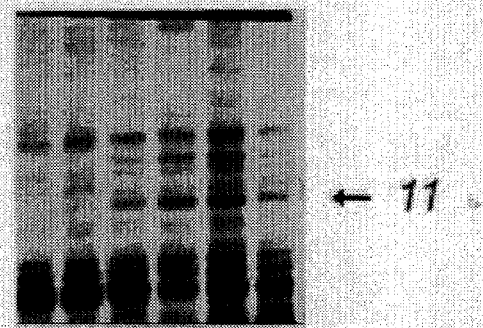
Figure 9C:
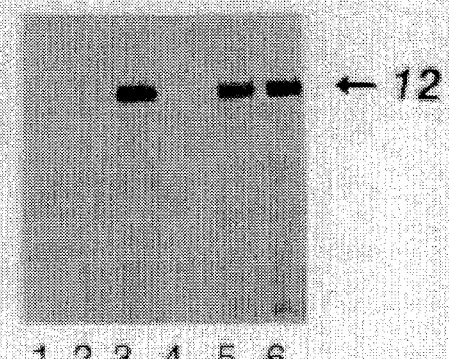

FIGS. 9A–9C are photographs of differential display gels comparing RNAs from syngeneic and allogeneic hearts. Total RNA was extracted from hearts after syngeneic (Lanes 1 and 2) and allogeneic (Lanes 3–6) transplantation and subjected to differential mRNA display analysis. Autoradiograms of amplified [γγ-$^{35}$S]dATP-labeled PCR products (after electrophoresis on 6% polyacrylamide gels) are shown for three different primer combinations (FIGS. 9A–9C) that identified four distinct fragments (arrows) upregulated in the allogeneic group. Primer combinations included $T_{12}VC$ as 3' primer for all reactions and various 5'-primers: FIG. 9A, OPA-16 (AGCCAGCGAA) (SEQ ID NO: 28); FIG. 9B, OPA-04 (AATCGGGCTG) (SEQ ID NO: 29); and FIG. 9C, OPA-14 (TCTGTGCTGG) (SEQ ID NO: 30). Lane 4 in FIG. 9A shows a PCR reaction that failed.

FIGS. 10A and 10B are photographs of RNA blot analyses confirming allograft-specific gene induction for Bands 1, 2, 11, and 12 identified initially by differential mRNA display. Total RNA (20 μg) obtained from syngeneic (Lanes 1 and 2) or allogeneic (Lanes 3–6) transplantations were hybridized with cDNA probes generated by PCR reamplification of bands recovered from differential display gels (FIG. 10A) or cloned cDNA fragments (FIG. 10B). Arrows indicate allograft-specific hybridization patterns. Arrowheads indicate hybridization in all six lanes (which was considered nonspecific). RNA loading (bottom panel) was evaluated by reprobing the same blot with the rat 36B4 homologue.

DETAILED DESCRIPTION

Lewis to F344 rat cardiac transplantation.

A rat heterotopic abdominal cardiac transplantation model was used to study transplant arteriosclerosis and cardiac rejection. (Cramer et al., 1993, supra; Adams, D. H., N. L. Tilney, J. J. Collins, and M. J. Karnovsky, 1992, Experimental graft arteriosclerosis. I. The Lewis-to-F344 allograft model, *Transplantation,* 53:1115–1119.) The combination of Lewis rat donors and F344 rat recipients results in long-term graft survival and a time-dependent development of arteriosclerotic lesions that resemble those in human transplant vessels on histologic examination (Cramer et al., 1993, supra; Adams et al., supra), and thus is a suitable animal model for this disease. Immunohistochemical studies using antibodies against monocytes, T-cells, and smooth muscle cells have shown that arteriosclerotic lesions develop in 3 distinct stages (Cramer, D. V., G. D. Wu, F. A. Chapman, E. Cajulis, H. K. Wang, and L. Makowka, 1992, Lymphocytic subsets and histopathologic changes associated with the development of heart transplant arteriosclerosis, *J. Heart Lung Transplant,* 11:458–466; Adams, D. H., L. R. Wyner, and M. J. Karnovsky, 1993, Experimental graft arteriosclerosis. II. Immunocytochemical analysis of lesion development, *Transplantation,* 56:794–799). In the first 30 days, the neointimal lesions are composed of infiltrating inflammatory cells (rather than smooth muscle cells), which are predominantly macrophages with fewer lymphocytes. Between 45 and 90 days, the infiltrating inflammatory cell population in the neointima decreases as intimal smooth muscle cells appear. In the last phase (beyond 90 days), the neointima is maximally expanded, often obliterative, and composed predominantly of smooth muscle cells with fewer infiltrating mononuclear cells. The early and persistent presence of monocytes/macrophages in the first stage of arteriosclerosis suggests a prominent role for the macrophage in the initial phase of chronic rejection. To date there are few studies examining specific molecular mechanisms that may regulate the infiltration or function of macrophages in chronically rejecting hearts.

Heterotopic abdominal cardiac transplantation was performed using Lewis donor hearts as described (Adams et al., supra) in an allogeneic combination involving F344 recipients. The syngeneic combination, involving Lewis recipients, was performed to assess the contribution of surgical manipulation to the inflammatory response. Lewis hearts that had been harvested but not transplanted were used as reference groups matching the strain of donor or grafted hearts. At the time of harvest, both the host (recipient) and the transplanted hearts were collected for histologic analysis and RNA extraction. The host heart served as a reference that had been exposed to the same circulation but was normal on histologic examination. In some studies, the host spleen was also harvested for a comparison of transcription patterns in an organ rich in inflammatory cells but free of local allogeneic stimulation.

Transplanted hearts were harvested at 7 and 14 days prior to the development of neointimal thickening. This strategy allowed the detection of transcriptional changes preceding functional changes. At the time of harvest, midventricular sections were taken for histologic analysis and snap frozen in liquid nitrogen for RNA extraction.

RNA isolation and Northern analysis.

Heterotopic abdominal cardiac transplantations were performed and samples were collected as described (Russell, M. E., Adams, D. J., Wyner, L., Halnon, N. J., Yamashita, Y. & Karnovsky, M. J., 1993, *Proc. Natl. Acad. Sci. USA*, 90:6086–6090; Adams, D. H., Tilney, N. L., Collins, J. J. & Karnovsky, M. J., 1992, *Transplantation*, 53:1115–1119, both of which are herein incorporated by reference). For allogeneic transplantations, Lewis rats were used as graft donors and F344 rats were used as recipients. Total cellular RNA was extracted from heart tissue with RNAzol B (Tel-Test, Friendwoods, Tex.) according to the manufacturer's instructions. Samples of total RNA (20 µg) were fractionated in 1% formaldehyde/agarose gels and transferred onto nylon-supported nitrocellulose (Micron Separation, Boston, Mass.) by standard capillary blotting techniques. Equivalent loading of samples was verified by ethidium bromide staining of the ribosomal bands. Specific probes were generated by labeling reamplified or cloned cDNA fragments with $[\alpha\text{-}^{32}P]$dCTP by using a random prime DNA labeling kit (Boehringer Mannheim Biochemicals, Chicago, Ill.). Nucleic acids were cross-linked to the membrane with ultraviolet light (Stratagene, Los Angeles, Calif.). Hybridization was completed with cDNA probes labeled with $^{32}P$ dCTP and the blots were washed under high-stringency conditions (0.2×SSC, 0.1% SDS at 60° C.). Blots were exposed to PhosphorImager screens at 25° C. or to Kodak X-Omat AR film with an intensifying screen at −70° C.

Differential mRNA display

Differential mRNA display analysis was carried out as described (Liang, P. & Pardee, A. B., 1992, *Science*, 257:967–971; Liang, P., Averboukh, L. & Pardee, A. B., 1993, *Nucl. Acids Res.*, 21:3269–3275, both of which are herein incorporated by reference), except that in vivo rather than in vitro samples were used and six rather than two samples were compared simultaneously, e.g. cDNA from 6 separate RNA populations representing 2 syngeneic hearts (normal on histologic examination) and 4 allografted hearts (with early indications of chronic cardiac rejection). Control studies included the substitution of water for cDNA or the omission of reverse transcriptase in the cDNA synthesis. The cDNA and PCR reactions were modified as follows. Total RNA (0.5 µg) was reverse transcribed in a 50-µl reaction using Superscript reverse transcriptase (Gibco-BRL Life Technologies, Baltimore, Md.) and the degenerate oligo dT primer, $T_{12}VC$ or $T_{12}VA$ (where V represented a mixture of dG, dA or dC) (Genosys, The Woodlands, Tex.). Control reactions were performed in the absence of reverse transcriptase. The cDNAs were then amplified by PCR in the presence of $[\gamma\text{-}^{35}S]$dATP on a Perkin Elmer 9600 thermal cycler, and control studies were performed in which water was substituted for cDNA. The reactions (20 µl) included arbitrary 10-mers (Kit A, Operon Technologies, Alameda, Calif.) as 5' primers and $T_{12}VC$ or $T_{12}VA$ as 3' primers. PCR parameters for the 40-cycle reaction were as follows: denaturation at 94° C. for 15 seconds, annealing at 40° C. for 60 seconds, and extension at 70° C. for 20 seconds. Radiolabeled PCR amplification products were analyzed using electrophoresis. Variability of 5–20% in the number and intensity of bands among given samples on repeated PCR analyses, as well as among different allogeneic or syngeneic samples in the same PCR analysis was observed. To confirm the reproducibility of amplification for selected bands, the reactions were repeated at least three times with different preparations of cDNA. Differentially upregulated bands were defined as those that were consistently present in all four allogeneic samples and absent in both syngeneic samples. Differentially downregulated bands were defined as those present only in syngeneic samples. PCR product bands were recovered from sequencing gels using electroelution and reamplified in a 40-cycle PCR reaction (80 µl) in the absence of isotope. Reamplified cDNAs ranging from 100 to 500 bp were used for cloning into plasmid vectors and as templates for random priming.

Cloning

Reamplified PCR products were directly cloned into the TA cloning vector PCR II (Invitrogen, San Diego, Calif.). The inserts were used as probes in Northern blot analysis of RNA from various cardiac allografts, syngrafts, and host hearts to confirm the allograft-specific hybridization pattern. The partial 3' cDNA fragment was then used to screen ~500,000 plaques from a bacteriophage lambda, custom Uni-ZAP cDNA library prepared from 14-day cardiac allograft poly(A)+RNA (Stratagene). Positive clones were isolated and rescued as plasmids, and their identity was verified by demonstration of allograft-specific hybridization on Northern blot analysis. DNA sequencing of both sense and anti-sense strands was performed with the Sequenase 2.0 kit (United States Biochemical, Cleveland, Ohio) on double-stranded plasmid DNA clones and subclones. Nucleotide and predicted amino acid-sequence searches of the GenBank and EMBL data bases were performed with the (FASTA program GCG software package).

Inflammatory cell populations

Isolated splenocytes were obtained by sieving splenic tissue into DMEM medium (Gibco-BRL Life Technologies, Baltimore, Md.) using methods well known in the art. These cells were fractionated with Ficoll-Paque (Pharmacia, Piscataway, N.J.), and the mononuclear fraction was cultured at a density of $2\text{--}4\times10^6$ cells/ml in a humidified incubator at 37° C. with 5% $CO_2$. A lymphocyte-enriched cell population was obtained by harvesting nonadherent cells by gentle washing 1 hour after plating. 20% of adherent cells stained with an anti-macrophage antibody, ED1, (Bioproducts, Inc., Indianapolis, Ind.) indicating an enrichment for phagocytic cells. In contrast, few of the nonadherent cells were ED1 positive.

Where indicated, lipopolysaccharide (1 ng/ml, Sigma, St. Louis, Mo.), rat interferon-γ, (100 U/ml, Gibco-BRL Life Technologies, Baltimore, Md.), concanavalin A (2 µg/ml, Sigma, St. Louis, Mo.) or buffer alone was added to isolated cell populations. The cells were harvested 3 hours later. Peritoneal inflammatory rat macrophages were elicited with thioglycolate medium using standard methods (Steinbeck, M. J., A. U. Khan, and M. J. Karnovsky, 1993, Extracellular production of singlet oxygen by stimulated macrophages quantified using 9,10-diphenylanthracene and perylene in a polystyrene film, *J. Biol. Chem.*, 268:15649–15654). Peritoneal exudate cells were collected 4 days after induction of inflammation, separated on a Ficoll-Paque gradient, and plated at a density of $2\times10^6$ cells/ml. At least 90% of the adherent cell population were judged to be macrophages by morphologic criteria and antibody staining. Total RNA was extracted from these isolated cells, the quality of which was assured by evaluation of ribosomal RNA after 1 μg had been separated on 3 mm agarose gels prior to cDNA preparation.

Quantitative reverse-transcription PCR assay

As an alternative to Northern blot analysis, a semiquantitative, reverse-transcription PCR analysis to compare Gal/GalNAc macrophage lectin transcript levels was performed to allow conservation of RNA when samples were limited. A reverse-transcription PCR technique developed to measure differences in monocyte chemoattractant protein-1 transcript levels (Russell et al., 1993 supra) was modified for use with Gal/GalNAc macrophage lectin. cDNA synthesis was completed with random primers (2.5 μg total RNA per reaction). Oligonucleotides were synthesized by Genosys, The Woodlands, Tex. The sequences were CCT AGA AAC CCT GAG AAC (SEQ ID NO: 31) for the 5' primer and GAG TGC CGC TTA TTG TAG (SEQ ID NO: 32) for the 3' primer, chosen from the sequence analysis of our cDNA clone to result in a 941-bp product. The thermal cycling parameters were denaturation at 94° C. for 15 seconds, annealing 54° C. for 20 seconds, and extension for 60 seconds (with a final extension of 7 minutes at the end of all cycles). For quantitative PCR analyses, 150,000 cpm of $^{32}$P-dCTP was included in the PCR reaction. The products were separated on 1% agarose gels which were dried and exposed to PhosphorImaging screens for 12 hours. The amount of incorporated $^{32}$P in amplified product bands was then measured by volume integration (Imagequant Software, Molecular Dynamics, San Francisco, Calif.).

To identify the optimum PCR conditions for accurate measurement of gene transcript levels, the linear assay range with respect to cycle number and starting template concentration was established by using different dilutions of cDNA. The measurement of Gal/GalNAc macrophage lectin transcript levels was then completed within these ranges (30 cycles, with starting cDNA dilutions of 1.25 μl). PCR amplification with G3PDH, a ubiquitously expressed gene, was used as a control to assess variations in total RNA or cDNA loading between samples. Corrected Gal/GalNAc macrophage lectin values were derived by dividing the measured amplified product value by the mean of the G3PDH value obtained for that cDNA from at least 3 analyses. PCR analyses were completed on each set of cDNAs at least 4 times. Results were subjected to analysis of variance (ANOVA) without replication. If a difference was significant, individual comparisons were made by the student's t test, corrected by the Bonferroni method. Although there were variations in absolute values derived from different experiments, relative differences between cDNA sets analyzed at the same time were preserved.

Comparison of corrected Gal/GalNAc macrophage lectin levels

Differences in corrected Gal/GalNAc macrophage lectin transcript levels were examined in 3 separate studies. The first study was completed to compare differences in transcript levels at various time points after cardiac transplantation. The 10 cDNAs in this time-course study included samples from 4 cardiac allografts harvested 7, 14, 28, and 75 days after transplantation compared with 1 day-0 Lewis heart, a total of 3 paired host hearts from days 7, 14, and 28, and a day-14 Lewis syngraft with its paired host heart. The second cDNA analysis examined whether Gal/GalNAc macrophage lectin induction occurred systemically or locally. cDNA levels in the host spleen (principal source of inflammatory cells) were compared with those in the allografted heart. The 6 cDNAs analyzed were derived from 2 allogeneic cardiac transplants: 1 harvested at 7 days, the other at 28 days. At each time point, the cDNAs from the host heart, allografted heart, and the host spleen were compared. In the third cDNA study, Gal/GalNAc macrophage lectin gene expression in various populations of isolated rat inflammatory cells was examined. Of the 9 cDNAs studied, 6 were prepared from splenocytes (both adherent and nonadherent, each type stimulated with buffer, concanavalin A, and lipopolysaccharide/interferon-γ), 2 from separate thioglycolate-elicited macrophage preparations, and 1 from a 14-day cardiac allograft.

In situ hybridization

In situ hybridization was completed as described (Arceci, R. J., A. A. J. King, M. C. Simon, S. H. Orkin, and D. B. Wilson, 1993, Mouse GATA-4: a retinoic acid-inducible GATA-binding transcription factor expressed in endodermally derived tissues and heart, *Mol. Cell. Biol.*, 13:2235–2246, herein incorporated by reference), using 5-micron frozen sections obtained from 7-day cardiac allografts and paired host hearts. To generate radiolabeled antisense and sense transcripts, the full-length 1.4-bp Bluescript cDNA was linearized and transcribed with T7 or T3 polymerase using $^{35}$S-UTP. The specificity of the antisense riboprobe was confirmed by hybridization in Northern analysis to 1.4-kb transcripts in lanes with cardiac allograft total RNA, but not in lanes with day-0 heart total RNA.

EXAMPLE 1

Methods of screening for differentially expressed genes involved in allograft rejection.

For most genes, expression is regulated at the level of transcription. Conventional measurements of mRNA transcript levels are usually confined to selected genes of interest and often require information about the gene sequence. In contrast, PCR-based differential display techniques circumvent this constraint by allowing comparison of gene expression patterns between two cell populations (Liang et al., 1992, supra) or between various murine organs (Welsh, J., Chada, K., Dalal, S. S., Cheng, R., Ralph, D. & McClelland, M., 1992, Nucl. Acids Res., 20:4965–4970). One of the principal advantages of differential display is that it permits the simultaneous identification of genes that are up- as well as downregulated. Thus differential display has the potential to identify a spectrum of molecular factors (known and unknown) that are differentially regulated in cells under various conditions.

Studies of allograft rejection in humans have been restricted by the limited availability of tissue for analysis. Clinical specimens are heterogenous in their degree of chronic rejection, their extent of superimposed disease processes, and the period between the time they are obtained and the time of transplantation. Also, transplanted hearts obtained at autopsy are not suitable for analysis (which requires viable tissue), and the utility of endomyocardial biopsy specimens is limited by their small size. Moreover, the restricted extent of arteriosclerotic lesions that follow transplantation suggests that the process is locally regulated; thus, studies measuring systemic levels of factors implicated in chronic rejection may not accurately reflect levels within the graft (Fyfe, A., Daly, P., Galligan, L., Pirc, L., Feindel, C. & Cardella, C., 1993, J. Am. Coll. Cardiol, 21:171–176).

Differential mRNA display

To identify transcriptionally regulated genes potentially involved in chronic rejection, differential mRNA display patterns for hearts from syngeneic transplantations were compared with those for hearts from allogeneic transplantations. Syngeneic hearts were normal on histologic examination, whereas 7- and 14-day allogeneic hearts showed luminal monocyte adhesion and infiltration without intimal thickening. PCR amplifications were performed with 27 primer combinations on all six samples and identified twelve PCR products, designated Bands 1–12. These bands were differentially expressed between allogeneic and syngeneic tissue. FIGS. 9A–9C show PCR amplifications obtained with three separate primer combinations. Four representative PCR products (Bands 1, 2, 11, and 12) were identified. These bands were reproducibly present in the allogeneic samples (Lanes 3–6), but not in the syngeneic samples (Lanes 1 and 2), in each of the three analyses identified (see FIGS. 9A–9C).

RNA blot analysis with PCR-amplified fragments

To confirm the gene regulation patterns observed in the differential display study, the twelve bands described above were recovered, reamplified, and used to probe RNA blots prepared with RNAs from syn- and allogeneic transplantations. When used as probes, four of the twelve PCR-amplified fragments (Bands 1, 2, 11, and 12) generated hybridization patterns that reproduced the allograft-specific increase in expression (FIG. 10A, Lanes 3–6). All four of these probes generated two hybridization signals of different sizes. The two signals identified by the Band-1 and -11 probes were both specifically present in allografted tissues (Lanes 3–6, arrows) and absent in syngrafted tissues (Lanes 1 and 2). In contrast, the Band-2 and -12 probes each generated one allograft-specific signal (arrows) reproducing the differential display pattern, as well as a second signal present in all six lanes (arrowheads) that did not reproduce the differential display pattern. Three reamplified PCR fragments hybridized nonspecifically to all six lanes. Five of the twelve cDNA probes did not detect any transcripts (data not shown). Such transcripts may not have been detected because their levels were below the sensitivity of the RNA blot analysis. As a control, RNA loading in all six lanes was confirmed by hybridization with the ribosomal reference gene 36B4 (Laborda et al., supra).

RNA Blot Analysis with Cloned Fragments

The PCR products that generated one or more allograft-specific hybridization patterns were then cloned and used as hybridization probes in RNA blot analysis to identify single clones corresponding to specific mRNA transcripts (FIG. 10B and Table 1). For Bands 2 and 12, individual cDNA clones were identified that produced hybridizations in an allograft-specific fashion. Identification of individual clones was more arduous for the bands that had generated two allograft-specific signals in the initial RNA blot analysis.

Two separate mechanisms account for the transcripts of two sizes observed for Band 1 compared with Band 11. For Band 1, an individual cDNA clone generated two faint hybridization signals of 3.5 kb and 1.5 kb specifically in the allograft samples (Lanes 3–6). This suggests that the two mRNAs were generated by alternative splicing of a common mRNA precursor, by a gene duplication event, or, less likely, by a common regulatory pattern for genes that share some homology. For Band 11, however, two independent cDNA clones with allograft-specific regulation were isolated: one hybridizing to a 1.0-kb transcript and the other to a 3.5-kb transcript. These two distinct clones hybridizing to transcripts of two sizes demonstrate that PCR-amplified products from a display band can contain a number of distinct cDNA fragments derived from different genes (Table 1). Thus, in the initial RNA blot screen, the PCR reamplified fragment (which may contain a mixture of PCR products) is more likely to identify differentially regulated transcripts than are individual cDNA clones.

Sequence homology

Cloned cDNA fragments that generated allograft-specific hybridization patterns in the RNA blot analysis were sequenced, and preliminary homology searches were performed. The results are summarized in Table 1. The cDNA fragment from Band 2 was found to be highly homologous to rat Gal/GalNAc lectin macrophage. The 382-bp fragment was 98% identical to bases 975–1357 of the published lectin sequence (Ii, M., Kurata, H., Itoh, N., Yamashina, I. & Kawasaki, T., 1990, J. Biol. Chem., 265:11295–11298). This region includes 114 bp of open reading frame as well as 3' untranslated sequences. Homologies with two distinct genes were identified for the two independent clones associated with Band 11. The cDNA fragment (110 bp) that hybridized to the smaller mRNA transcript (1.0 kb) was 79% homologous to the 3' untranslated region of a partial cDNA sequence obtained from a mouse ubiquitin-like gene (Kumar, S., Tomooka, Y. & Noda, M., 1992, Biochem. Biophys. Res. Commun., 185:1155–1161). The cloned fragment (119 bp) that hybridized to the larger transcript (3.5 kb) was 92% homologous to a partial cDNA sequence of the mouse nuclear P1 gene (Hershko, A. & Ciechanover, A., 1992, Annu. Rev. Biochem., 61:761–807). The homologous region of the P1 gene was located within the open reading frame (bases 1–120) and not at the 3' end. Therefore, in this instance, the 3' primer of the initial PCR reaction hybridized to an internal sequence. To date no significant homology with any published gene for the sequences obtained from the Band-1 and -12 cDNA fragments has been found, suggesting that they represent previously unknown genes associated with chronic cardiac rejection.

Each differential display analysis was performed at least three times to reduce nonspecific (background) PCR signal interference, and the selection of cDNA bands chosen for further study was restricted to those that reproduced the regulation pattern of the first RNA blot analysis in at least three analyses.

Using 27 primer combinations, twelve differential display cDNA bands that were reproducibly up- or downregulated in allogeneic hearts were identified. For four of the twelve bands, this allograft-specific regulation was reproduced on RNA blot analysis. Two unknown genes and three known genes not previously implicated in chronic rejection were identified.

The screening methods of the invention are designed to identify mediators that might be selective for or specific to chronic rejection. Three known genes never before associated with transplant rejection and two novel genes have been identified using the methods of the invention. The three upregulated genes with identifiable homologies correspond to the Gal/GalNAc macrophage lectin, the nuclear P1 gene, and a ubiquitin-like gene.

The link between the macrophage lectin gene and chronic rejection is important because, prior to the invention, the factors responsible for macrophage accumulation in the early phase of the process were not known. Lectins are cell-surface molecules that mediate cell-cell interactions by recognizing specific sugar molecules on adjacent cells (Sharon et al., supra). The murine Gal/GalNAc-specific lectin was originally identified by immunofluorescence on thioglycolate-elicited and OK-432 (a streptococcal antitumor preparation)-activated macrophages but not on unstimulated or resident macrophages (Oda et al., 1989, supra), suggesting that this lectin may be a marker of macrophage activation.

The mouse P1 protein, a homologue of yeast MCM3 (minichromosome mutant), plays a role in the initiation of DNA replication in association with DNA polymerase primase (Thoemmes, P., Fett, R., Schray, B., Burkhart, R., Barnes, M., Kennedy, C., Brown, N. C. & Knippers, R., 1992, Nucl. Acids Res., 20:1069–1074). The identification of elevated transcript levels for the P1 gene in cardiac allografts compared with syngrafts suggests the presence of replicating cells at early points in chronic rejection. Localizing the specific cell type that expresses P1 gene transcripts (or protein) by in situ hybridization or immunohistochemistry may help elucidate early proliferative processes in chronic rejection.

The third known gene upregulated in cardiac allografts is homologous to the 3' region of a murine ubiquitin sequence (Kumar et al., supra). As its name implies, ubiquitin is expressed in all eukaryotic cells. However, ubiquitin gene transcripts appear to be upregulated specifically in allogeneic tissue. Although ubiquitin is involved in a wide variety of regulatory functions within the cell, its role in protein degradation is best understood. In that process ubiquitin is covalently attached to a specific protein target which is then recognized and degraded (Hershko et al., supra). The conjugation of ubiquitin to a protein is essential to normal protein turnover. However, the induction of ubiquitin is also part of the cellular response to stress, damage, or injury (Mayer, R. J., Arnold, J., Laszlo, L., Landon, M. & Lowe, J., 1991, Biochim. Biophys. Acta, 1089:141–151). Although ubiquitin's specific role in chronic cardiac rejection is not clear, it is possible that ubiquitin is involved in the response to immune injury thought to initiate allograft arteriosclerosis.

Advantages

The screening methods of the invention can be used to identify mediators associated with chronic allograft rejection, a complex, multicellular disease process using differential display technology to detect upregulated or downregulated allograft gene transcripts. Differential display technology has been used to study breast cancer (Liang et al., 1992, supra; Liang et al., 1993, supra; Liang, P., Averboukh, L., Keyomarsi, K., Sager, R. & Pardee, A. B., 1992, Cancer Res., 52:6966–6968; Sager, R., Anisowicz, A., Neveu, M., Liang, P. & Sotiropoulou, G., 1993, FASEB J., 7:964–970). However, in contrast to the breast-cancer studies, which compared two populations of in vitro cell lines at once, the screening methods of the invention compare whole tissue from allogeneic transplantations (where chronic rejection develops) with whole tissue from syngeneic transplantations (where rejection is absent). One important advantage of this approach is that the pathophysiologic environment associated with the chronic disease process is preserved. The invention provides a method of analyzing a mixture of both resident and infiltrating cells, as well as the complex network of regulatory stimuli that may have been impossible to reproduce in isolated cells in vitro (Liaw, L. & Schwartz, S. M., 1993, Arterioscler. Thromb., 13:985–993). Also, because the screening method can compare a number of tissue samples at once, e.g., a series of six transplanted hearts simultaneously, the identification of factors that might be related to a single animal or procedure rather than to the disease itself can be avoided.

With the identification of these five candidate mediators of chronic rejection, utility of the screening methods of the invention, e.g., those which utilize differential mRNA display analysis, to identify molecular factors associated with complex multicellular processes, has been demonstrated. For identification of allograft-specific factors, an increase or decrease in allograft gene transcript of at least 4 times the amount of corresponding syngraft gene transcript is preferable.

In the case of chronic rejection, which affects the donor organ only and spares host organs, differential mRNA display can be used to examine the transplanted heart as well as its infiltrating cell populations. Given that inflammatory cells are often activated in a manner specific to their microenvironment, the power of this technique resides in its preservation of infiltrating cells and the complex network of regulatory influences in the tissue under investigation. In vitro systems investigating single cell types cannot reproduce the spectrum of interactions present in diseased tissue in vivo because they lack the counterregulatory effects of neighboring cells. The differentially regulated factors identified in this manner are therefore more likely to be of direct clinical relevance. Finally, the methods of the invention allow the identification of candidate factors that may be beyond the scope of established theories of chronic rejection.

EXAMPLE 2

Assays to diagnose rejection of an allograft.

As described above, several genes (Gal/GalNAc-macrophage lectin, AIF-1, AIF-2, ubiquitin and P1) which are differentially expressed in the allograft have been identified using the screening methods of the invention. Other genes can be identified using the same methods. Having identified genes which are differentially expressed in an allograft compared to a syngraft, detection of expression of these genes either at the level of transcription, e.g., by PCR, Northern blot, differential mRNA display, or in situ hybridization, or at the level of translation/protein production, e.g., by FACS, Western blot, or in situ immunostaining, provides a valuable tool for early and reliable diagnosis of transplant rejection. For example, Gal/GalNAc macrophage lectin transcript or protein levels in transplanted heart samples obtained by endomyocardial biopsy could serve as clinical markers of macrophage infiltration. These levels might provide prognostic information about the degree of chronic rejection or the rate at which arteriosclerosis is progressing.

One of the major advantages of such a diagnostic approach is that the screening methods of the invention allow early detection of events which lead to allograft rejection, and thus facilitate early intervention to prevent or inhibit rejection of the transplanted organ. Another advantage is that the diagnostic methods of the invention can be performed on a very small amount of tissue which may be obtained using standard biopsy techniques known in the art.

EXAMPLE 3

Therapeutic applications for differentially expressed allograft genes.

As described above, an increase in the amount of an allograft gene transcript compared to the corresponding syngraft gene transcript indicates that the allograft transcript encodes a mediator of allograft rejection. Thus, allograft rejection in patients may be decreased or inhibited using gene therapy in which the antisense strand of the upregulated gene is introduced into the cells in which the gene is transcribed. The antisense strand (either RNA or DNA) may be directly introduced into the cells in a form that is capable of binding to the transcripts, or a vector containing sequence which, once within the target cells, is transcribed into the appropriate antisense mRNA, may be the species administered to the patient's cells. Antisense nucleic acid which hybridizes to the complementary coding strand of DNA can decrease or inhibit production of the polypeptide product encoded by the upregulated allograft gene, by associating with the normally single-stranded mRNA transcript, and thereby interfering with translation.

In addition to gene therapy, polypeptides of the invention may be useful to block activity of the differentially expressed allograft polypeptide, e.g., by blocking binding of the polypeptide to its ligand.

The isolated DNA of the invention may be introduced into target cells of the patient by standard vectors and/or gene delivery systems. Suitable gene delivery systems may include liposomes, receptor-mediated delivery systems, naked DNA, and viral vectors such as herpes viruses, retroviruses, and adenoviruses, among others.

A therapeutic composition is provided which includes a pharmaceutically acceptable carrier and a therapeutically effective amount of a nucleic acid which is capable of inhibiting expression of the allograft gene, either directly or by encoding a transcript which inhibits expression of the gene. The therapeutic composition may also include a gene delivery system as described above. Pharmaceutically acceptable carriers are biologically compatible vehicles which are suitable for administration to an animal: e.g., physiological saline. A therapeutically effective amount is an amount of the DNA of the invention which is capable of producing a medically desirable result in a treated animal, e.g., downregulation of the differentially expressed allograft gene.

As is well known in the medical arts, dosages for any one patient depends upon many factors, including the patient's size, body surface area, age, the particular compound to be administered, sex, time and route of administration, general health, and other drugs being administered concurrently. Dosages for the compounds of the invention will vary, but a preferred dosage for intravenous administration is from approximately $10^6$ to $10^{22}$ copies of the nucleic acid molecule.

EXAMPLE 4

AIF-1 and AIF-2.

As described above, the screening methods of the invention were used to identify two novel genes which are upregulated in rat cardiac allografts with transplant arteriosclerosis. Transcript levels for two novel genes, AIF-1 and AIF-2, were found to be increased in rat cardiac allografts undergoing chronic rejection. In cardiac allograft tissue, AIF-1 gene transcripts localized to inflammatory cells in macrophage-rich regions.

A full-length cDNA clone (651 bp) has been obtained for one of these transcripts, AIF-1 (SEQ ID NO:4). The predicted amino acid sequence of the longest open reading (147 amino acids) (SEQ ID NO:5) contains a 12-amino acid region similar to the EF-hand ($Ca^{2+}$-binding) domain. The AIF-1 clone specifically hybridized to RNA isolated from allografts (7, 14, 28, and 75 days after transplantation) and spleens by Northern analysis. Semiquantitative PCR studies showed elevated AIF-1 transcript levels in splenic and peritoneal macrophages, balloon-injured carotid arteries with neointimal thickening, and allografts. By in situ hybridization, AIF-1 transcripts localized to areas of mononuclear cell infiltration in cardiac allografts. The localization within cardiac allografts of a mononuclear-cell subset expressing AIF-1 transcripts suggests that AIF-1 may act as an inflammatory mediator in chronic rejection and arteriosclerosis.

Further evidence that AIF-1 and AIF-2 are genes expressed in macrophages comes from the observation that gene transcripts for both are present in the spleen (and not in other organs) and from in vitro studies with isolated rat macrophage populations.

In the differential mRNA display analysis, AIF-1 and AIF-2 were found to represent cDNA fragments upregulated in all 4 allogeneic (Lewis to F344) hearts (with early signs of chronic rejection) compared with two control syngeneic (Lewis to Lewis) hearts exposed to the same surgical procedure but histologically normal. These cDNA fragments were used to confirm the allograft-specific gene expression pattern in additional transplantations.

Identification and characterization of AIF-1 and AIF-2 gene transcripts

The Lewis to Fisher rat transplantation model of arteriosclerosis was used to obtain in vivo specimens with chronic rejection and differential display technology used to identify transcriptionally induced as described above. Bands 1 and 12 (see FIGS. 9A–9C) were harvested, reamplified, and used as probes in Northern analysis. The allograft-specific induction pattern was confirmed in the RNA extracted from the original 6 samples identifying gene transcripts of 0.7 kb. Following Northern blot confirmation, partial cloning, sequence analysis of AIF-1 (331 bp sequenced/400 bp fragment) (SEQ ID NO:1), and a homology search were completed. Partial cloning, sequence analysis, and a homology search were also completed for AIF-2 (359 bp/~450 bp sequenced) (SEQ ID NO:2, 3). A database search using these fragments revealed no alignment with known sequences.

A search using a larger fragment revealed alignment for the AIF-1 cDNA over most of its length compared with sections of a 38.5 kb cosmid genomic segment of the HLA class III region (which included the human BAT2 gene) (Iris, et al., 1993, *Nature Genetics* 3:137–145). This cosmid was one of three generated by Iris et al. in an effort to examine a 90-kb HLA class III segment. It has now been demonstrated that 6 sections of HLA class III cosmid aligned with over 568 bp of the 651-bp AIF-1 cDNA, with homology ranging from 68% to 93%.

However, the area homologous to AIF-1 was found 3 kb upstream of the human BAT2 sequence; thus it is unlikely that the cDNA is actually related to BAT2. Rather, the AIF-1 cDNA appears to represent an as yet undescribed HLA class III gene. Furthermore, Iris et al. did not identify further coding sequences but referred to work by other investigators, Sargent, et al., 1989, *The EMBO Journal* 8:2305–2312. Sargent et al. studied transcription units in the HLA class III region and identified a transcription unit approximately 3.0 kb upstream from the BAT2 gene that hybridized to transcripts in U937 cells (human monocyte-like cell line) and MOLT-4 (a human T cell line) but not HepG2 (hepatoma cell line) or RAJI (B cell line). However, it has now been found that AIF-1 transcripts are not present in U937 cells, suggesting that AIF-1 is not related to the transcription unit that was described but not sequenced or submitted to sequence databases. AIF-1 transcripts were also not detected by reverse transcription-PCR in HL60 cells (human promyelocytic leukemia cell line).

AIF-1 Gene Expression Studies

Gene expression studies using the full-length cDNA in Northern analysis have shown hybridization to 0.7-kb transcripts in cardiac allografts (7-, 14-, 28-, and 75-day old) but not the paired host hearts. In situ hybridization localized AIF-1 mRNA to inflammatory infiltrates within cardiac allografts. Organ blot analysis examining 13 organs demonstrated strong hybridization patterns in normal splenic tissue and testes and faint hybridization in Peyer's patches, brain, and some lung samples. AIF-1 hybridization was not observed in liver, lung, adrenal gland, uterus, kidney, skeletal muscle, ovary, salivary gland, or intestine.

Northern blots containing samples from murine organs were probed with the rat AIF-1 cDNA. Hybridization to transcripts of two sizes was detected in murine testes (~2.0 kb and ~1.7 kb).

Semiquantitative reverse transcription PCR showed increased transcript levels in adherent splenocytes (macrophage enriched) compared with nonadherent splenocytes, elicited peritoneal macrophages, and bone marrow-derived macrophages. In addition, transcript levels were increased in balloon-injured rat carotid arteries with neointimal thickening.

Using in situ hybridization, anti-sense AIF-1 riboprobes hybridized to inflammatory infiltrates in cardiac allografts, as seen by the increase in the number of silver grains in comparison with neighboring myocytes and other noninflammatory cells. No significant hybridization was seen in host hearts or when the sense probe was used on cardiac allograft sections. Southern analyses revealed that AIF-1 cDNA strongly hybridized to blots containing digested genomic human and murine DNA.

Searches against the Prosite protein database using the AIF-1 polypeptide sequence were negative. However, a profile scan protein motif database search identified an AIF-1 region (amino acids 49 to 77) with homology to the EF-hand calcium-binding domain. At position 69 (the residue believed to be important for calcium binding), AIF-1 contains Ser instead of Asp or Glu, raising the possibility that this AIF-1 region may not be involved in calcium binding.

AIF-2 Gene Expression Studies

The 2.2-kb cDNA fragment identified up to 3 transcripts (1.5 bp, 3.5 bp, >8.0 kb) in various rat cardiac allografts (day 7, 14, 28) and spleens (but not in the other 8 organs examined). Gene transcript levels measured by reverse transcription PCR indicated that AIF-2 was found in inflammatory cells enriched in macrophages (adherent splenocytes, peritoneal macrophages, a rat pulmonary alveolar macrophage cell line, and bone-marrow macrophages). Preliminary studies indicated that transcript levels in bone-marrow macrophages increased after stimulation with interferon-gamma (IFN-γ) alone or with the combination of IFN-γ and lipopolysaccharide (LPS).

Cloning of full-length cDNA from custom-made rat cardiac allograft cDNA library

A rat cardiac allograft cDNA library was obtained from Stratagene, Inc. To isolate the full-length cDNAs, the 14-day old cardiac allograft cDNA library was screened with the partial cDNA fragments identified in the differential display. Fifteen AIF-positive phagemid clones were obtained; however, eight were identical in sequence. The full-length AIF-1 cDNA (SEQ ID NO:4) was found to be 651 bp in length and contain a 70-bp 5' untranslated region, a continuous open reading frame (longest open reading frame 441 bp), and a 140-bp 3' untranslated region that included one potential polyadenylation sequence. The first ATG was located at base 71. Translation of the open reading frame predicted a 147-amino acid polypeptide with a predicted molecular mass of 16.8 kDa. Charged amino acids comprised 35% of the predicted polypeptide without any cysteines. A hydrophilic profile was predicted from the plot generated using the Kyte and Doolittle algorithm. This plot revealed the absence of any hydrophobic stretches, suggesting that AIF-1 is not a membrane-spanning protein.

Only partial cDNAs derived from the 3' end of the gene have been obtained for AIF-2 (see SEQ ID NOs:2,3,8–27). The remaining 5' sequences can be obtained with further screening of the cardiac allograft library, using known methods employing probes derived from the previously cloned and sequenced 3' fragments. In addition to further screening of the library, PCR amplification of 5' cDNA ends can be accomplished using 5'-RACE (Rapid Amplification of cDNA ends)-Ready™ cDNA and the 5' AmpliFINDER™ RACE Kit from Clontech, Inc. Using this cloning strategy, random hexamers are used for cDNA synthesis, followed by ligation of a modified single-stranded anchor oligonucleotide to the 3' end of the first-strand cDNA. Nested AIF-2 primers derived from the 3' end of the gene and a 5' primer complementary to the anchor can then be used to progressively amplify the remaining 5' end of the gene.

Clinical applications

As described above, measurements of gene transcript or polypeptide product levels may serve as clinical or diagnostic indicators of macrophage infiltration, chronic inflammation, transplant rejection, and arteriosclerosis. AIF-1 may be used to identify subsets of macrophages given that in situ hybridization studies show that transcripts are expressed by only some of the macrophages in the cardiac allograft. All or part of the DNAs of the invention, e.g., AIF-1 DNA with the sequence of SEQ ID NO:1 or 4 or the AIF-2 DNA with the sequence of SEQ ID NO:2, 3, 8, 9, 10, 11, 12, 13, 14, 15, 16, 17, 18, 19, 20, 21, 22, 23, 24, 25, 26, or 27, can be used as hybridization probes to identify AIF-1 or AIF-2, respectively, for the purpose of diagnosing transplant rejection. Portions of these DNAs can also be used as PCR primers to amplify AIF-1 or AIF-2 sequences to identify expression of these genes in allografts for the purpose of diagnosing rejection, using e.g., differential display technology. The DNA of SEQ ID NO:1 or 4 can also be used as a reliable transcriptional marker for macrophages.

Administration of AIF-1 or AIF-2 polypeptides or antibodies which bind to either AIF-1 or AIF-2 may modulate the inflammatory response by blocking cell infiltration, migration, activation, or macrophage effector functions. Macrophages have a broad number of effector functions (antigen presentation, parasitic and viral killing, phagocytosis, tumor clearance) which could be impaired by blocking AIF-1 or AIF-2. All or part of the DNAs of the invention, e.g., AIF-1 DNA with the sequence of SEQ ID NO:1 or 4 or the AIF-2 DNA with the sequence of SEQ ID NO:2, 3, 8, 9, 10, 11, 12, 13, 14, 15, 16, 17, 18, 19, 20, 21, 22, 23, 24, 25, 26, or 27, can be cloned into an expression vector and used to produce polypeptides of AIF-1 or AIF-2 for the purpose of immunizing animals to generate polyclonal or monoclonal antibodies. Such antibodies can then be use for therapeutic applications as described above or for diagnostic applications such as identification of AIF-1 or AIF-2 polypeptides in allografts indicating ongoing transplant rejection.

Also, fusion proteins of AIF-1 or AIF-2 containing components known to block specific inflammatory factors (see Other Embodiments) may also serve as a way of modulating the inflammatory response.

In addition to these therapeutic applications, valuable animal models to study allograft rejection can be made by producing transgenic animals (e.g., mice, rats, rabbits, guinea pigs, hamsters, dogs, goats, horses, cows, pigs, or sheep) in which the genes encoding AIF-1 or AIF-2 are deleted or overexpressed using methods known in the art. Such transgenic animals could serve as models of an impaired inflammatory response for research studies aimed at elucidating the pathophysiologic process.

EXAMPLE 5

Gal/GalNAc macrophage lectin Characterization of Gal/GalNAc macrophage lectin as a mediator of transplant rejection.

Disclosed herein is the first demonstration of an in vivo role of Gal/GalNAc macrophage lectin in a pathologic state-chronic cardiac rejection. Of particular interest is the unique localization of the expressed gene to the allograft, a degree of compartmentalization not heretofore reported in rejecting organs. By also demonstrating the upregulation of Gal/GalNAc macrophage lectin in association only with inflammatory macrophages elicited with thioglycolate, the data detailed below further substantiate that local activation of inflammatory cells plays a role in the phenomenon of chronic rejection. Taken together, these findings suggest that Gal/GalNAc macrophage lectin, a marker of inflammatory macrophages, is likely to be one of the factors that mediate the recruitment or adhesion of macrophages in chronic cardiac rejection.

Lectins are a family of cell-surface proteins that specifically and selectively bind to complex carbohydrates on apposing cells (Sharon, N. and H. Lis., 1989, Lectins as cell recognition molecules, *Science*, 246:227–234). They have emerged as primary markers for cell recognition with clear functional roles. For example, interference with a lectin's binding to its apposing carbohydrate can disrupt bacterial and mononuclear cell attachment, tumor metastasis, and embryogenesis. Gal/GalNAc macrophage lectin falls into the category of C-type animal lectins characterized by calcium-dependent activity, extracellular location, and absence of free thiols. The murine lectin has been purified in an effort to identify the factor responsible for the tumor binding capacity it conferred to murine macrophages after stimulation with the antitumor streptococcal preparation OK-432 (Oda et al., 1988, supra; Oda et al., 1989, supra). Antibody against the murine lectin prevented macrophage binding to and killing of tumor cells. Kawasaki et al. cloned rat macrophage lectin, which these researchers designated macrophage-asialoglycoprotein-binding protein (m-ASGP-BP), and performed comparisons with the extensively studied rat hepatic lectins (RHL) (Ii et al., supra; Kawasaki, T., M. Ii, Y. Kozutsumi, and I. Yamashina, 1986, Isolation and characterization of a receptor lectin specific for galactose/N-acetylgalactosamine from macrophages, *Carbohydr. Res.*, 151:197–206; Ii, M., T. Kawasaki, and I. Yamashina, 1988, Structural similarity between the macrophage lectin specific for galactose/N-acetylgalactosamine and the hepatic asialoglycoprotein binding protein, *Biochem. Biophys. Res. Commun.*, 155:720–725). Single-chain m-ASGP-BP was shown to form homooligomeric receptors that bind and internalize ligand in a high-affinity fashion specific for Gal and GalNac (Ozaki, K., M. Ii, N. Itoh, and T. Kawasaki, 1992, Expression of a functional asialoglycoprotein receptor through transfection of a cloned cDNA that encodes a macrophage lectin, *J. Biol. Chem.*, 267:9229–9235). Rat hepatic lectin is an endocytic receptor for deglycosylated serum glycoproteins. The major form, RHL1, has a 59% homology with the macrophage lectin cDNA. The 2 minor forms, RHL2 and -3, have 45% homologies. An interesting variation in the macrophage lectin protein is the 24 amino-acid insertion that includes an Arg-Gly-Asp or RGD sequence. RGD is an integrin recognition sequence, raising the possibility that Gal/GalNAc macrophage lectin also confers integrin mediated cellular adhesion.

Mechanisms regulating monocyte/macrophage recruitment are of great interest in understanding pathophysiologic processes (Valente, A. J., M. M. Rozek, E. A. Sprague, and C. J. Schwartz, 1992, Mechanisms in intimal monocyte-macrophage recruitment. A special role for monocyte chemotactic protein-1, *Circulation*, 86:III-20-III-25). A spectrum of cell-surface molecules or receptors is believed to control macrophage function. For example, cytokine receptors, such as the receptor for interferon-γ, modulate the activation of macrophages; integrin receptors, such as CD11a/CD18, regulate integrin adhesion; and the mannose receptor, a macrophage lectin, is involved in endocytosis. Gal/GalNAc macrophage lectin may also fall into this category, given that it is specifically and locally upregulated in the context of a pathophysiologic process where the hallmark is monocyte/macrophage infiltration and arteriosclerosis. More studies are required to identify the functional role of Gal/GalNAc macrophage lectin and to clarify the carbohydrate ligand on apposing cells such as allograft cells. By analogy with other lectins, it is possible that Gal/GalNAc macrophage lectin is also involved in the recognition of macrophages by exposed carbohydrates, and in their localization or adhesion to injured or stimulated donor tissue.

Differentially expressed Gal/GalNAc macrophage lectin

Figure 1A:
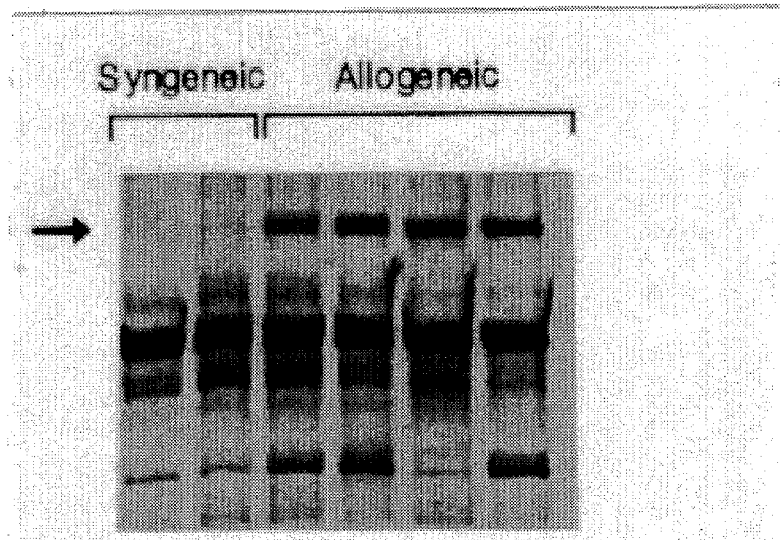
FIG. 1A is a photograph of a differential mRNA display gel showing an upregulated PCR fragment in chronically rejecting hearts produced by allogeneic cardiac transplantation. The 6% polyacrylamide gel electrophoretic analysis of randomly amplified PCR products shows a cDNA fragment identified in the 4 heart samples obtained after allogeneic transplantation (allografts) but not in the 2 hearts obtained after syngeneic transplantation (syngrafts).
Figure 1B:
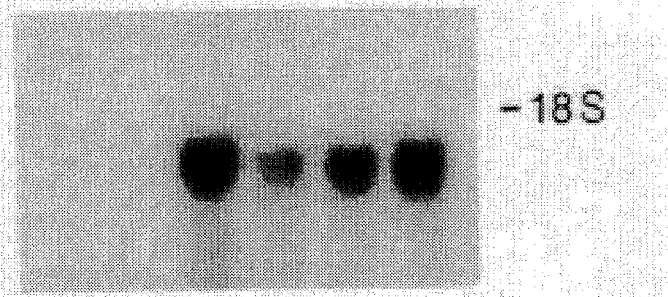
FIG. 1B is a photograph of a Northern blot. The upregulated PCR fragment was harvested and reamplified from the differential display gel shown in FIG. 1A. When radiolabeled with $^{32}$P and used as a probe in Northern analysis, the fragment hybridized to 1.4-kb transcripts found only in the 4 lanes containing the hearts subjected to allogeneic transplantation, which develop chronic rejection (lanes 3–6), but not to the 2 hearts from syngeneic cardiac transplantation (lanes 1 and 2). Samples from the same total RNA extraction were used in both the PCR and Northern analyses.
Figure 1C:
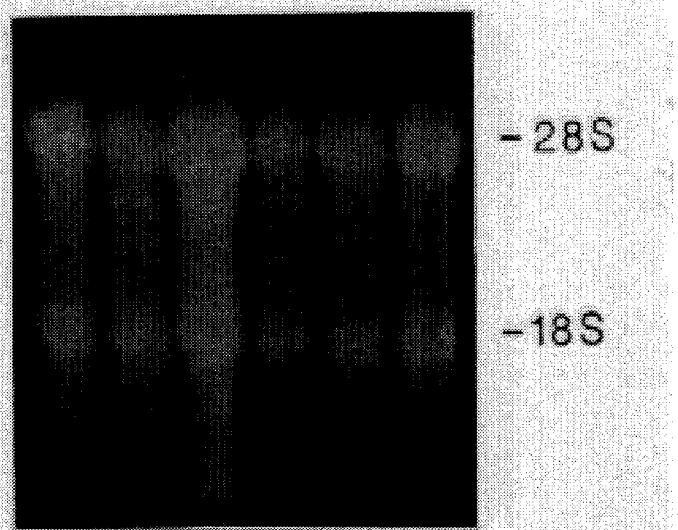
FIG. 1C is a photograph of a RNA gel stained with ethidium bromide before transfer to a fiber membrane, to demonstrate that 20 μg of total RNA was loaded into each lane.
Figures 2A, 2B:
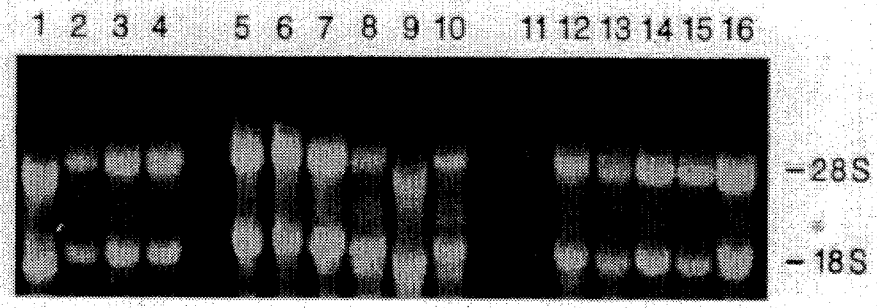
FIG. 2A is a photograph of a Northern blot analysis showing upregulation of transcripts in an expanded series of 7- and 14-day cardiac allografts, but not in paired host hearts. Northern blot analysis using the transplanted heart (cardiac allograft) and host heart (exposed to the same circulation but histologically normal) from an additional 2 syngeneic and 6 allogeneic cardiac transplantations confirmed and extended the allograft-specific induction patterns. PCR-amplified DNA fragment from the differential display study hybridized to 1.4-kb transcripts found only in allogeneic transplanted hearts harvested at 7 and 14 days (lanes 5–7 and 14–16) but not to transcripts from the paired host hearts or syngeneic transplanted hearts.
FIG. 2B is a photograph of a RNA gel stained with ethidium bromide before transfer, to demonstrate that 20 μg of total RNA was loaded into each lane (with the exception of lane 11).

Analysis of polyacrylamide gels containing randomly amplified PCR products obtained by using OPA 4 (AAT CGG GCT G) (SEQ ID NO:29) as a 5' primer and $T_{12}VTC$ (where V included A, C, and G ) as a 3' primer identified an ~380-bp fragment in sample lanes from allogeneic hearts but not in those from syngeneic hearts (FIG. 1A). When the cDNA in these upregulated bands was harvested, reamplified, and used to probe Northern blots, an allograft-specific hybridization pattern was visible (FIG. 1B). Transcripts of 1.4 kb were identified in lanes 3 through 6, containing total RNA derived from 4 hearts after allogeneic transplantation, but not in lanes 1 and 2, containing RNA from 2 syngeneic transplants. RNA loading prior to transfer is shown in the ethidium-stained agarose gel (FIG. 1C). These findings confirmed the gene regulation pattern identified in the differential mRNA display analysis performed with the same panel of total RNAs. Northern analysis was then completed with total RNA obtained from an additional 6 allogeneic transplantations (3 each harvested at 7 and 14 days) and 2 syngeneic transplantations (both harvested at 14 days). FIG. 2 shows a strong hybridization to 1.4-kb transcripts in all 6 lanes (lanes 5–7 and 14–16) containing allografted heart samples, in contrast with the 6 paired host-heart samples and 4 syngeneic-heart samples (2 hosts and 2 syngrafts). Taken together (FIGS. 1 and 2), these findings indicate that the induction was not restricted to individual animals or procedures but occurred uniformly in Lewis to F344 cardiac transplantation.

Cloning of Gal/GalNAc macrophage lectin from a rat cardiac cDNA library

Direct cloning of the amplified PCR fragment harvested from the differential display gel produced a 380-bp insert. When this insert was used as a probe in Northern blot analysis, it hybridized to transcripts of 1.4-kb (data not shown) in lanes containing RNA from cardiac allografts but not in lanes containing samples from the host hearts, again reproducing the pattern identified by the differential display analysis. To determine the identity of the full-length cDNA, a cardiac allograft cDNA library (Stratagene, La Jolla, Calif.) was screened with the 380-bp cloned PCR fragment. Nine recombinants were identified, the largest of which was 1.4 kb. Sequence analysis of this fragment and homology searching revealed that the fragment was 99% homologous to rat Gal/GalNAc-macrophage lectin mRNA (GenBank accession number J05495). The J05495 cDNA had been cloned from a rat peritoneal macrophage cDNA library.

Figures 3A, 3B:
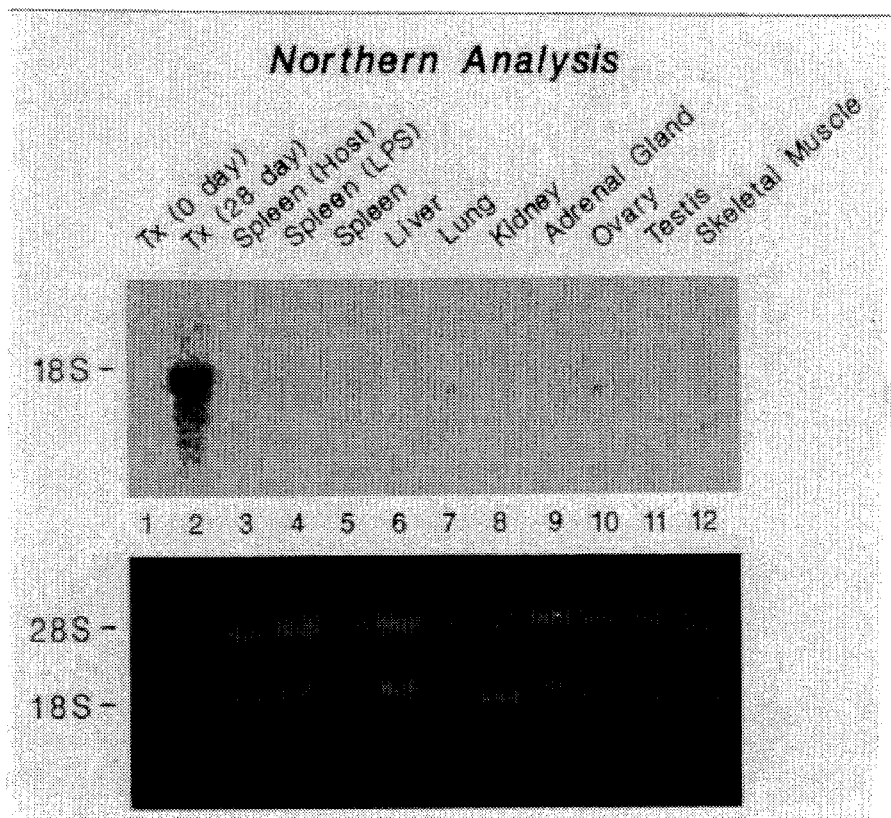
FIG. 3A is a photograph of a Northern blot analysis of RNA from rat organs using the full-length Gal/GalNAc macrophage lectin cDNA as a probe. Tissue-specific upregulation was observed in cardiac allografts. The full-length cDNA was isolated from a rat cardiac allograft cDNA library and used as a probe in Northern blot analysis completed with 20 μg/lane total RNA from the indicated organs. The cDNA probe hybridized strongly to 1.4-kb transcripts in the 28-day cardiac allograft sample. In contrast, hybridization levels were low in all other organs examined, including those rich in resident monocytes and macrophages. To examine possible changes in expression related to systemic effects of inflammatory stimulation, the paired host spleen and a spleen harvested 8 hours following intraperitoneal lipopolysaccharide injection were included.
FIG. 3B is a photograph of a RNA gel stained with ethidium bromide before transfer, to demonstrate that each lane contains 20 μg of total RNA.

Characterization of Gal/GalNAc macrophage lectin gene expression with a full-length cDNA clone Northern blot analysis was used to examine the specificity of Gal/GalNAc macrophage lectin gene expression in a variety of rat organs, particularly those known to contain various resident mononuclear cells. Probing with full-length Gal/GalNAc macrophage lectin cDNA, strong hybridization was observed only in lane 2 containing RNA from the 28-day cardiac allograft (FIG. 3). A sample from the host spleen (lane 3) was included in the assay to determine whether Gal/GalNAc macrophage lectin transcripts were induced by a systemic effect on macrophages after transplantation. The sample from the spleen of a rat 8 hours after intraperitoneal treatment with lipopolysaccharide (lane 4) was included to determine whether this potent inflammatory stimuli would alter Gal/GalNAc macrophage lectin expression in the spleen. A control spleen sample (lane 5) harvested without any stimulation was also included. All 3 samples from spleens showed faint to no hybridization, even though spleens are the principal source of macrophages. Similarly, hybridization signals were not apparent in the lanes containing RNA from other organs including the liver (lane 6), which contains Kupffer cells, lung (lane 7), which contains alveolar macrophages, kidney (lane 8), adrenal gland (lane 9), ovary (lane 10), testes (lane 11) and skeletal muscle (lane 12). This restricted pattern of Gal/GalNAc macrophage lectin expression suggests that its induction is specific to and localized within the cardiac allograft.

Reverse-transcription PCR measurement of Gal/GalNAc macrophage lectin transcript levels To achieve greater sensitivity in measuring Gal/GalNAc macrophage lectin transcripts, a reverse transcription-PCR assay was developed using specific primers. PCR conditions were established to insure a linear amplification rate to avoid an amplification plateau in which the PCR product level is no longer proportional to the starting template level. Gal/GalNAc macrophage lectin gene amplification (FIG. 4) was linear over 8 PCR cycles (upper panel) and by more than 2 logs in initial template or cDNA concentration (represented as the calculated amount of cDNA in the PCR reaction) (lower panel). These ranges are consistent with those typically found in PCR assay systems. For subsequent comparisons of Gal/GalNAc macrophage lectin gene transcript levels in various sets of cDNAs, PCR amplification of the control gene, G3PDH, was performed to derive corrected or normalized levels. This approach was used to compare relative differences between samples from three separate cDNA panels.

Specific and localized increase in corrected Gal/GalNAc macrophage lectin levels in cardiac allografts FIG. 5 shows that corrected Gal/GalNAc macrophage lectin gene transcript levels increased significantly in cardiac allografts (black bars) at all time points studied (day 7, 14, 28, and 75) in comparison with the 3 reference groups: a day-0 heart (black bar), paired host hearts (hatched bars) and a syngraft (stippled bar) (P<0.008). Differences in transcript levels between the various allograft time points were not significant. This lack of a difference suggests that there was no further increase after the initial induction, which would be consistent with an ongoing or chronic stimulation. To examine whether Gal/GalNAc macrophage lectin gene induction was systemically or locally regulated, levels in cardiac allografts were compared with those in host spleens (given that the spleen would be a major source of macrophages but free of direct exposure to stimuli in allografted tissue). As seen in FIG. 6, Gal/GalNAc macrophage lectin levels increased significantly in the 7- and 28-day cardiac allografts (black bars) relative to host spleens and hearts (hatched bars) (P<0.0001). The low transcript levels in the host spleens suggest that Gal/GalNAc macrophage lectin gene induction in the cardiac allograft is due to local activation or stimulation.

Corrected Gal/GalNAc macrophage lectin transcript levels in isolated inflammatory macrophages Transcript levels were measured in various types of isolated rat inflammatory cells to confirm the macrophage-specific nature of Gal/GalNAc gene expression. FIG. 7 shows that corrected transcript levels increased significantly in thioglycolate-elicited macrophages and cells from a 14-day cardiac allograft (P<0.0001) compared with adherent (macrophage-enriched) splenocytes (stimulated with buffer, concanavalin A, and lipopolysaccharide/interferon-γ) and nonadherent (lymphocyte-enriched) splenocytes (stimulated with buffer, concanavalin A and lipopolysaccharide/interferon-γ). The identification of Gal/GalNAc macrophage lectin gene transcripts only in thioglycolate-elicited rat macrophages, an inflammatory macrophage population, extends the observation that antibody against the murine lectin binds only to stimulated murine macrophages (Oda, S., M. Sato, S. Toyoshima, and T. Osawa, 1988, Purification and characterization of a lectin-like molecule specific for galactose/N-acetyl-galactosamine from tumoricidal macrophages, *J. Biochem.* (Tokyo), 104:600–605).

In situ localization of Gal/GalNAc macrophage lectin mRNA in cardiac allografts

In situ hybridization was performed to localize the cell types expressing Gal/GalNAc macrophage lectin transcripts in cardiac allograft tissue. Positive hybridization with the antisense Gal/GalNAc probe was visible in scattered mononuclear cells within inflammatory infiltrates in the interstitium and perivascular space (FIG. 8A and 8B), as demonstrated by the clustering of silver grains (arrows). There was little hybridization to adjacent noninflammatory cells such as cardiac myocytes, or when the negative control, sense Gal/GalNAc probe (FIG. 8C and 8D) was used in seriate sections. There was no significant hybridization of either the antisense or sense probe to paired host hearts, which lacked inflammatory infiltrates (not shown).

Restricted upregulation of Gal/GalNAc macrophage lectin

The gene transcripts of Gal/GalNAc macrophage lectin were found to be specifically localized to and upregulated within Lewis to F344 rat cardiac allografts. Increases in Gal/GalNAc macrophage lectin gene transcript levels occurred early (by 7 days) during initial macrophage accumulation and were sustained (through 14, 28, and 75 days), as would be expected for a chronic inflammatory state characterized by ongoing macrophage infiltration. In contrast, transcript levels were low in 3 reference groups: paired host hearts (exposed to the same circulation but normal on histologic examination), day-14 Lewis syngrafts (subject to the same surgical procedure but with matching host and recipient strains), and day-0 Lewis hearts (harvested but not transplanted). Furthermore, the induction of Gal/GalNAc macrophage lectin gene transcripts occurred in a compartmental fashion restricted to the allografted tissue. Transcript elevation was not found in the matching host spleens (studied because they are the principal source of macrophages but not subject to allogeneic stimulation), nor was it found in other organs rich in resident macrophages. This pattern is in keeping with the arteriosclerotic changes found in cardiac transplants, which affect donor vessels but spare host vessels. Using in situ hybridization, a subset of inflammatory cells (presumably macrophages) within the cardiac allograft was shown to express Gal/GalNAc macrophage lectin transcripts. In examining the specificity of Gal/GalNAc macrophage lectin gene expression in various isolated rat inflammatory cells, transcripts were found to be present only in exudative or thioglycolate-elicited macrophages. Taken together, these results show that Gal/GalNAc macrophage lectin gene expression is restricted in vivo to a subset of infiltrating inflammatory cells in cardiac allografts and in vitro to inflammatory macrophages, suggesting that this lectin is an inducible factor under tight regulatory control.

Gal/GalNAc macrophage lectin is of particular importance in chronic rejection because in vitro studies suggest that its surface expression increases markedly on activated macrophages, and that it regulates the binding to and destruction of tumor cells by macrophages (Oda, S., M. Sato, S. Toyoshima, and T. Osawa, 1989, Binding of activated macrophages to tumor cells through a macrophage lectin and its role in macrophage tumoricidal activity, *J. Biochem.* (Tokyo), 105:1040–1043). These data raise the possibility that Gal/GalNAc macrophage lectin may also play a role in the vascular changes that occur in chronic cardiac rejection by regulating the infiltration of macrophages within the allografts.

Cloning human Gal/GalNAc macrophage lectin

The existence of a human homologue was suggested by Southern analysis using digested human genomic DNA which demonstrated cross hybridization with the rat Gal/GalNAc macrophage lectin cDNA.

Using primers derived from the rat Gal/GalNAc macrophage lectin DNA sequence, a PCR product was amplified from human cardiac transplant biopsy tissue. This product co-migrated with the PCR product amplified from rat tissue. The human PCR product was then isolated and used as a template for PCR reactions using a different 5' primer based on the rat sequence and the same 3' primer. A PCR product of the predicted size was generated. This series of PCR reactions using two separate and distinct 5' primers suggests that the human homologue of rat Gal/GalNAc macrophage lectin was present and detectable using rat primers.

DNA fragments derived from the rat Gal/GalNAc macrophage lectin cDNA sequence or PCR fragments amplified from the human template can be used as hybridization probes to screen for overlapping cDNA inserts in a cDNA library prepared from cells previously determined, e.g., by Northern blot, to express transcripts which bind to rat probes. The screening of cDNA libraries with radiolabelled cDNA probes is routine in the art of molecular biology (see Sambrook et al., 1989, *Molecular Cloning: a Laboratory Manual*, second edition., Cold Spring Harbor Press, Cold Spring Harbor, N.Y).

The human cDNA can be isolated and subcloned into a plasmid vector (e.g., pBluescriptII), and the plasmid DNA purified by standard techniques. The cDNA insert can be sequenced using the dideoxy chain termination method well known in the art (Sambrook et al, supra). Oligonucleotide primers corresponding to bordering vector regions as well as primers prepared from previously isolated cDNA clones can be employed to progressively determine the sequence of the entire gene.

DNA containing a sequence that encodes part or all of the amino acid sequence of Gal/GalNAc macrophage lectin can be recloned into an expression vector, using a variety of methods known in the art. For example, a recombinant polypeptide can be expressed as a fusion protein with maltose binding protein produced in *E. coli*. Using the maltose binding protein fusion and purification system (New England Biolabs), the cloned human cDNA sequence can be inserted downstream and in frame of the gene encoding maltose binding protein (malE), and the malE fusion protein can then be overexpressed. In the absence of convenient restriction sites in the human cDNA sequence, PCR can be used to introduce restriction sites compatible with the vector at the 5' and 3' end of the cDNA fragment to facilitate insertion of the cDNA fragment into the vector.

Following expression of the fusion protein, it can be purified by affinity chromatography. For example, the fusion protein can be purified by virtue of the ability of the maltose binding protein portion of the fusion protein to bind to amylose immobilized on a column.

To facilitate protein purification, the pMalE plasmid contains a factor Xa cleavage site upstream of the site into which the cDNA is inserted into the vector. Thus, the fusion protein purified as described above can then be cleaved with factor Xa to separate the maltose binding protein from recombinant human cDNA gene product. The cleavage products can be subjected to further chromatography to purify recombinant macrophage lectin from the maltose binding protein.

The purified recombinant gene product can then be used to raise polyclonal or monoclonal antibodies against the human macrophage lectin using well-known methods (see Coligan et al., eds., *Current Protocols in Immunology*, 1992, Greene Publishing Associates and Wiley-Interscience). To generate monoclonal antibodies, a mouse can be immunized with the recombinant protein, and antibody-secreting B cells isolated and immortalized with a non-secretory myeloma cell fusion partner. Hybridomas are then screened for production of lectin-specific antibody and cloned to obtain a homogenous cell population which produces a monoclonal antibody.

Identification of compounds which inhibit allograft rejection

A screening method for identifying compounds capable of inhibiting the association of Gal/GalNAc macrophage lectin with its carbohydrate ligand may be carried out as follows:

A cell which expresses Gal/GalNAc macrophage lectin is provided. The cell is most preferably a macrophage, e.g., cell lines, such as J744A.1 (ATCC T1B67) or RAW264.7 (ATCC T1B71) for murine studies, or primary cells such as bone marrowed derived macrophages, but may be any type of cell which expresses Gal/GalNAc macrophage lectin on its surface (e.g., a cell transfected with a cDNA encoding the lectin). Alternatively, Gal/GalNAc lectin may be provided immobilized, e.g., linked to an agarose or acrylamide bead. The lectin is incubated in the presence of a candidate compound. A reference point could be established under standard conditions and the results from any assay compared to the pre-established standard as the control. The lectin is then allowed to bind to labeled carbohydrate ligand, and the resulting complex is washed to remove unbound ligand. The complexes can then be recovered, and subjected to SDS-PAGE. A reduction in the amount of label associated with the complex in the presence of candidate compound compared to that in the absence of candidate compound (or compared to a pre-established standard) indicates that the candidate compound inhibits Gal/GalNAc macrophage lectin-mediated allograft rejection.

An in vitro binding assay may also be accomplished as follows. Modifications of the frozen section assay originally described by Stamper and Woodruff (Stamper, et al., 1977, *J. Immunol.*, 119:772–780, Butcher, et al., 1979, *J. Immunol.*, 123:1996–2003, herein incorporated by reference), can be used to study the role of Gal/GalNAc macrophage lectin in adhesion to rat cardiac allografts. Inflammatory cells demonstrated to express the lectin such as thioglycolate-elicited peritoneal macrophages or T cell-stimulated bone marrow derived macrophages (Gessl, et al., 1989, *J. Immunol.*, 142:4372–4377), herein incorporated by reference) can be labeled with the fluorescent dye 1,1'-dioctadecyl-3,3,3, 3'-tetramethylindocarbocyanaine percholate. Labeled macrophages can be incubated with frozen tissue sections from rat cardiac allografts. Conditions can be optimized to maximize specific calcium dependent adhesion to the allograft and control heart sections by variation in temperature, incubation buffer, and washing. Adherent cells can be quantitated using methods known in the art. Specificity of the adherence can be evaluated by measuring the extent of inhibition with a given candidate compound, such as, anti-lectin antibody, Gal-bovine serum albumin (BSA) or GalNAc-BSA conjugates, or recombinantly expressed or modified Gal/GalNAc macrophage lectin polypeptides.

Screening for inhibitors can also be accomplished in vivo. For example, the organ to be allografted can be perfused or soaked in a solution containing a candidate compound prior to transplantation. The organ can then transplanted and monitored for indications of rejection. Transplant rejection can be monitored using conventional methods, e.g., sacrifice of the animal followed by gross examination of the tissue and histological studies, as well as the diagnostic assays of the invention, e.g., evaluating a tissue biopsy for the differential expression of an allograft gene, e.g., Gal/GalNAc macrophage lectin. A decrease in gene expression or a reduction in the physical characteristics of transplant rejection would indicate that the candidate compound inhibits allograft rejection.

Inhibition of allograft rejection by blocking binding of Gal/GalNAc macrophage lectin to Gal/GalNAc The development of inhibitors (peptides, antibodies, or, carbohydrates) that block the lectin-carbohydrate interaction could provide a means of attenuating macrophage infiltration within allografts and disrupting the associated cytokine cascades believed to be initiated by macrophage activation.

Carbohydrates such as Gal or GalNAc, as well as compounds containing Gal or GalNAc, can be used to block binding of Gal/GalNAc macrophage lectin to its ligand on the surface of cells in the allografted tissue, an event that may contribute to the eventual rejection of the allografted tissue or organ.

Soluble polypeptides and fragments thereof, e.g., polypeptide containing a carbohydrate-binding fragment of Gal/GalNAc macrophage lectin, can be used to block the association of macrophage lectin with its carbohydrate ligand.

The term "fragment", as applied to a polypeptide, herein denotes a peptide of at least 10 amino acids. The polypeptide fragments of the invention are preferably at least 20 contiguous amino acids, more preferably at least 40 contiguous amino acids, even more preferably at least 50 contiguous amino acids, and most preferably at least about 80 or more contiguous amino acids in length. Such peptides can be generated by methods known to those skilled in the art, including proteolytic cleavage of the protein, de novo synthesis of the fragment, or genetic engineering, e.g., cloning the gene or a portion of the gene encoding Gal/GalNAc macrophage lectin into an expression vector as described above.

Also within the invention are analogs of the above peptides. Analogs can differ from the peptides encoded by differentially expressed genes, e.g., Gal/GalNAc macrophage lectin or a carbohydrate-binding fragment thereof, by conservative amino acid replacements which alter the sequence but do not adversely affect the functioning of the resulting polypeptide, or by modifications which do not affect the sequence, or by both. Modifications (which do not normally alter primary sequence) include in vivo or in vitro chemical derivitization of polypeptides, e.g., acetylation or carboxylation. Also included are modifications of glycosylation, e.g., those made by modifying the glycosylation patterns of a polypeptide during its synthesis and processing or in further processing steps, e.g., by exposing the polypeptide to enzymes which affect glycosylation, e.g., mammalian glycosylating or deglycosylating enzymes.

The invention includes analogs in which one or more peptide bonds have been replaced with an alternative type of covalent bond (a "peptide mimetic") which is not susceptible to cleavage by peptidases. Where proteolytic degradation of the peptides following injection into the subject is a problem, replacement of a particularly sensitive peptide bond with a noncleavable peptide mimetic will make the resulting peptide more stable and thus more useful as a therapeutic. Such mimetics, and methods of incorporating them into polypeptides, are well known in the art. Similarly, the replacement of an L-amino acid residue with a D-amino acid residue is a standard way of rendering the polypeptide less sensitive to proteolysis. Also useful are amino-terminal blocking groups such as t-butyloxycarbonyl, acetyl, theyl, succinyl, methoxysuccinyl, suberyl, adipyl, azelayl, dansyl, benzyloxycarbonyl, fluorenylmethoxycarbonyl, methoxyazelayl, methoxyadipyl, methoxysuberyl, and 2,4,-dinitrophenyl.

Peptides may be administered to the patient intravenously in a pharmaceutically acceptable carrier such as physiological saline. Such methods are well known to those of ordinary skill in the art. The formulations of this invention are useful for parenteral administration, such as intravenous, subcutaneous, intramuscular, intraperitoneal, and inhalation.

OTHER EMBODIMENTS

Hybrid inhibitors of allograft rejection in which a first portion that blocks lectin-carbohydrate binding, e.g., a carbohydrate-binding fragment of Gal/GalNAc macrophage lectin, is linked to a second portion which decreases macrophage-mediated destruction of transplanted tissue, can be constructed using methods known in the art. The first portion can be covalently linked to the second portion, for example, by ligating DNA encoding the first portion in frame with DNA encoding the second portion into an expression vector, and recombinantly producing the hybrid inhibitor. The first portion may be a compound which blocks Gal/GalNAc macrophage lectin binding to Gal/GalNAc, such as a carbohydrate-binding fragment of Gal/GalNAc macrophage lectin, or an antibody or antibody fragment which is lectin-specific or carbohydrate-specific. The first portion of the hybrid may also be an AIF-1 or AIF-2 polypeptide. The second portion of the hybrid can be a compound which is capable of blocking inflammatory cell (e.g., macrophage) infiltration, migration, activation, or other effector functions, such as interleukin-10, transforming growth factor β-1, D-mannosidase, or migration inhibition factor.

TABLE 1

Analysis of cDNA fragments identified by differential mRNA display

| Band | Expression pattern | | Transcript Size | Sequence Homology |
|---|---|---|---|---|
| | Differential Display | Northern Analysis | | |
| 1 | allogeneic | allogeneic | 3.5 kb | no homology* |
| | | allogeneic | 1.5 kb | no homology* |
| 2 | allogeneic | allogeneic | 1.4 kb | rat Gal/GalNAc macrophage lectin |
| | | nonspecific | 1.0 kb | not sequenced |
| 3 | allogeneic | nonspecific | 1.8 kb | not sequenced |
| 4 | syngencic | no hybridization | | |
| 5 | allogenetc | no hybridization | | |
| 6 | allogeneic | no hybridization | | |
| 7 | allogeneic | no hybridization | | |
| 8 | allogeneic | no hybridization | | |
| 9 | syngeneic | nonspecific | 1.0 kb | not sequenced |
| 10 | allogeneic | nonspecific | 1.6 kb | not sequenced |
| 11 | allogeneic | allogeneic | 3.5 kb | mouse P1 protein |
| | | allogeneic | 1.0 kb | mouse ubiquitin-like protein |
| 12 | allogeneic | nonspecific | 5.0 kb | not sequenced |
| | | allogeneic | 0.7 kb | no homology |

*Single cDNA clone hybridized to transcripts of two sizes.

TABLE 2

SEQ ID NO: 1

| | | | | |
|---|---|---|---|---|
| GCTGCTGTCA | TTAGAAGGTC | CTCGGTCCCA | CCGTGTTATA | TCCACCTCCA |
| ATTAGGGCAA | TACAGAAATA | GCTTTCTTGG | CTGGGGACC | AGTTGGCTTC |
| TGGTGTTCTT | TGTTTTTCTC | CTCACACATC | AGAATCATTC | TCAAGATGGC |
| AGATCTCTTG | CCCAGCATCA | TTCTGAGAAA | GTCAGAGTAA | CTGAACGTCT |
| CCTCGGAGCC | ACTGGACACC | TCTCTAATTA | ATTTCTTCAG | CTCTAGATGG |
| GTCTTGGGAA | CCCAAGTTTC | TCCAGCATTC | GCTTCAAGGA | CATAATATCG |
| ATATCTCCAT | TGCCATTCAG | ATCAACTCAT | G | |

TABLE 3

SEQ ID NO. 2

| | | | | | | | | | | | | | | |
|---|---|---|---|---|---|---|---|---|---|---|---|---|---|---|
| ACG | AGA | ATA | TGG | CTG | TAA | TCT | GGA | GGA | CAT | CAT | TGT | TGT | TCT | GGG |
| CCC | TTC | AGT | GGG | ATC | TGC | TGC | TTT | ACC | TTC | CAG | AGA | ATC | AGC | AAC |
| CTC | ATT | TAC | CAA | GTT | CAT | CTG | TGT | GTG | AGA | ACG | TTG | ACT | | |

TABLE 4

SEQ ID NO. 3

| | | | | |
|---|---|---|---|---|
| TTTTTTTTTT | TTGCAGCCAT | TGTAGAAGGA | TACGGGAAGC | ATTTATCGAA |
| AATTCCAGAC | AAGAACCTCA | TTCTCTAAGG | GATATGAAGC | CTATCTGTGT |
| ACCGAAGTTA | AGGCCATCAC | GGACATGGGA | GAAAAACTTC | TCAGGATGGC |
| AAGATGTGCA | GAGGTCAAGA | TCTTCCTCCT | GGTCTTGAAT | ATCTGTGGAA |
| GAATTCCTCC | TGCTTCTAGA | GATCCTGTGC | TTTTCGGATG | TCAACGTAGG |
| GATTTGGTGA | GTCAAACTGT | CTCACACACG | AAGGATGAAC | ATTGTGAAAT |
| GAGGTTGCTG | ATCTCTGG | | | |

TABLE 5

SEQ ID NO. 4

| | | | | |
|---|---|---|---|---|
| GAGGAGCCAG | CCAACACACT | GCAGCCTCAT | CGTCATCTCC | CCACCTAAGG |
| CCACCAGCGT | CTGAGGAGCT | ATGAGCCAGA | GCAAGGATTT | GCAGGGAGGA |
| AAAGCTTTTG | CACTGCTGAA | AGCCCAGCAG | GAAGAGAGGT | TGGATGGGAT |
| CAACAAGCAC | TTCCTCGATG | ATCCCAAGTA | CAGCAGTGAT | GAGGATCTGC |
| AGTCCAAACT | GGAGGCCTTC | AAGACGAAGT | ACATGGAGTT | TGATCTGAAT |
| GGCAATGGAG | ATATCGATAT | TATGTCCTTG | AAGCGAATGC | TGGAGAAACT |
| TGGGGTTCCC | AAGACCCATC | TAGAGCTGAA | GAAATTAATT | AGAGAGGTGT |
| CCAGTGGCTC | CGAGGAGACG | TTCAGTTACT | CTGACTTTCT | CAGAATGATG |
| CTGGGCAAGA | GATCTGCCAT | CTTGAGAATG | ATTCTGATGT | ATGAGGAGAA |
| AAACAAAGAA | CACCAGAAGC | CAACTGGTCC | CCCAGCCAAG | AAAGCTATTT |
| CTGAGTTGCC | CTAATTGGAG | GTGGATATAA | CACGGTGGGA | CCGAGGACCT |
| TCTAATGACA | GCAGCATGGG | AAAAGAAGAA | GCAGTTGTGA | GCCAGAGTCA |
| AACTAAATAA | ATAATGCTCC | CTAGTGCAAA | AAAAAAAAAA | AAAAAAAAA A |

TABLE 6

SEQ ID NO. 5

| | | | | | | | | | | | | | |
|---|---|---|---|---|---|---|---|---|---|---|---|---|---|
| Met | Ser | Gln | Ser | Lys | Asp | Leu | Gln | Gly | Gly | Lys | Ala | Phe | Gly | Leu |
| Leu | Lys | Ala | Gln | Gln | Glu | Glu | Arg | Leu | Asp | Gly | Ile | Asn | Lys | His |
| Phe | Leu | Asp | Asp | Pro | Lys | Tyr | Ser | Ser | Asp | Glu | Asp | Leu | Gln | Ser |
| Lys | Leu | Glu | Ala | Phe | Lys | Thr | Lys | Tyr | Met | Glu | Phe | Asp | Leu | Asn |
| Gly | Asn | Gly | Asp | Ile | Asp | Ile | Met | Ser | Leu | Lys | Arg | Met | Leu | Glu |
| Lys | Leu | Gly | Val | Pro | Lys | Thr | His | Leu | Glu | Leu | Lys | Lys | Leu | Ile |
| Arg | Glu | Val | Ser | Ser | Gly | Ser | Glu | Glu | Thr | Phe | Ser | Tyr | Ser | Asp |
| Phe | Leu | Arg | Met | Met | Leu | Gly | Lys | Arg | Ser | Ala | Ile | Leu | Arg | Met |
| Ile | Leu | Met | Tyr | Glu | Glu | Lys | Asn | Lys | Glu | His | Gln | Lys | Pro | Thr |
| Gly | Pro | Pro | Ala | Lys | Lys | Ala | Ile | Ser | Glu | Leu | Pro | | | |

TABLE 7

| SEQ. ID NO. 6 | |
|---|---|
| CACATCTTGC CATCCTGA | 5 |

TABLE 8

| SEQ ID NO. 7 | |
|---|---|
| CATGGTGCTT GAGAACAG | 10 |

TABLE 9

| SEQ ID NO. 8 | | | | |
|---|---|---|---|---|
| GTTTAATGCA | GAGAAATTTT | ACCGAATAAA | GACTGATCAC | GCCAGGTAAG |
| TATGGGTAAT | GGGGAAGAAG | GAGCCTGAAT | CTTACGATGG | AATAATTACA |
| AATCAGAGAG | GAATCACAAT | CACAGCTCTT | GGCGCAGACT | GTATACCTAT |
| AGTCTTTGCA | GATCCTGTGA | AAAAAGCATG | TGGGGCTGCT | CACTCGGGCT |
| GGAAGGGCAC | TTTGTTGGGC | GTCGCTATGG | CTACTGTGAA | TGCTATGATA |
| GCAGAATATG | GCTGTAATCT | GGAGGACATC | ATTGTTGTTC | TGGGCCCTTC |
| AGTGGGATCT | | | | |

25

TABLE 10

| SEQ ID NO. 9 | | | | |
|---|---|---|---|---|
| TTTTTTTTTC | TTATATATAA | ATTCTAACCT | TTAATGTTTA | TGTAAACATA |
| CATGTATATG | GCTATGTAAA | TCTGTGGGTA | TAAGTGTGGA | TAGGTGTTGA |
| AACTAGAAAG | GGAACATAAA | AGGGGATTGT | GCAAGGGAGA | ACAAAACACA |
| TGAGACAGGA | AAGAGGGGCT | TCTGCAGTGA | AAGGGTACAC | AAGGGGCCAG |
| GGAAAGGGAG | AGCGAGGGCC | AGAAAAACAT | GGTGCTTGAG | AACAGCATAA |
| GGAACCTGTA | TTTATAAGGC | AGTT | | |

TABLE 11

| SEQ ID NO. 10 | | | | |
|---|---|---|---|---|
| CCGAGTCTCG | CGTCTACCAG | AGCTGCAAGA | TGTCTGTGCT | CCCTGGAATA |
| ATTGTCCTTG | TGGGACGATC | CTCATGTGCC | TGGTGTGCCT | GCTTGCTAGT |
| AGGAGGAATA | ATACCGGTTC | ATTCTCCTAC | CGGAACACCA | ATATGTATAT |
| GTGCATCGGC | CCCAAGTCAT | CATTGAAAAC | ACAGTGTTCT | CAAGTGGACA |
| AGACCTTCAC | TGGATTGTTC | AAGAGAGATC | CAGCCTTACA | AGAAGGAAAA |
| CTAGAGACCA | AAATAAATCC | TCTTCCTTCT | CGATGGGTAT | CATCTGCTTC |
| TTCTTCCTAA | AAGACTGGGG | GAGCTATCTC | TCATAGTGAG | TACATTCAGT |
| GTGCAAGTGG | CTCTCAGAGT | AGACTCAGTC | CTTGCTTG | |

TABLE 12

| SEQ ID NO. 11 | | | | |
|---|---|---|---|---|
| TCGAGTTTTT | TTTTTTTTTT | TTTATATATA | AATTCTAACC | TTTAATGTTT |
| ATGTAAACAT | ACATGTATAT | GGCAATGTAA | ATCTGTGGGT | ATAAGTGTGG |
| ATAGGTGTTG | AAACTAGAAA | GGGAACATAA | AAGGGGATTG | TGCAAGGGAG |
| AACAAAACAC | ATGACAGGAA | AGAGGGGCTT | CTGCAGTGAA | AGGGTACACA |
| AGGGGCCAGG | GAAAGGGAGA | GCGGAGGGCC | AGAAAAACAT | GGTGCTTGAG |
| AACAGCATAA | GGAAACCTGT | ATTTTATAAG | GCAGTTAAAA | TATACATTTA |
| AAAGGAACG | | | | |

TABLE 13

SEQ ID NO. 12

| | | | | |
|---|---|---|---|---|
| TTTTTTTTTT | TTTTTTTTTT | TTTTTTTTTT | CTTATATATA | AATTCTAACC |
| TTTAATGTTT | ATGTAAACAT | ACATGTATAT | GGCTATGTAA | ATCTGTGGGT |
| ATAAGTGTGG | ATAGGTGTTG | AAACTAGAAA | GGGAACATAA | AAGGGGATTG |
| TGCAAGGGAG | AACAAAACAC | ATGAGACAGG | AAAGAGGGGC | TTCTGCAGTG |
| AAAGGGTACA | CAAGGGGCCA | GGGAAAGGGA | GACGGAGGGC | CAGAAAAACA |
| TGGTGCTTGA | GAACAGCATA | AGGAAACCTG | GTATTTTATA | AGGCAGTTAA |
| AAATATACAT | TTAAAAGGAA | ACGTTTATCT | CCCCTACTGC | ATTTGATTCA |
| AATGAGAAGG | TG | | | |

TABLE 14

SEQ ID NO. 13

| | | | | |
|---|---|---|---|---|
| GAAAAAGGTG | CCTGACTGAA | GAATGGCAGA | AGCAGTCTTG | ATAGATCTCT |
| CTGGTTTACA | ATTGAACTCT | CAGGAAAACT | GTCATCAGAT | GGTACTGAAG |
| ACGCTGGATG | GTATTCACGA | CCACCATGCC | CCCAAGGCCA | AGTTCCTTTG |
| TATAATATGT | TGCAGCGATG | CCACCAATGG | AAAGGGTGGG | GAATATGGCC |
| TCTGTGAACT | GGAAGCAGGA | AATGGCTTTT | CAAGTCTCGC | GGGAAAATTC |
| GAGACTGTTA | GCCATCCAGC | CTGGCTGCCT | CTTTGTATTC | AGTAAACAA |
| AAATAGATGA | GGAGGATCTG | AGCCGCGTTA | AGGTGATTGT | GCCCGAG |

TABLE 15

SEQ ID NO. 14

| | | | | |
|---|---|---|---|---|
| TTTTTTTTTT | TTTTTTTTTT | TTTTTTTTTT | TTTTTTTTTT | ACATACACAC |
| AGTATTTTAT | TTAGCCATAA | TGAAATTATC | AAACTTATAG | GAAAAATTGA |
| TGGATCTGGA | ATTATTTAT | ATGAGCAAAA | TAATCCAGAC | TCAGAATAAG |
| AAACACCACA | TGTTCTTTCT | TATATATAAA | TTCTAACCTT | TAATGTTTAT |
| GTAAACATAC | ATGTATATGG | CTATGTAAAT | CTGTGGGTAT | AAGTGTGGAT |
| AGGTGTTGAA | ACTAGAAAGG | GAACATAAAA | GGGGATTGTG | CAAGGGAGAA |
| CAAAACATAT | GAGACAGGAA | AGAGGGGCTT | CTGTAGTGAA | AGGGTACCAA |

TABLE 16

SEQ ID NO. 15

| | | | | |
|---|---|---|---|---|
| TCTCAGCTCA | CTCAATCTTT | TCAGTAGTTC | CAAACGGAGA | GATCCCAAAG |
| TGGTTGTTCA | AGAAAACCTC | CGCGGCCTGG | CAAATGCTGC | AGGGTTTAAT |
| GCAGAGAAAT | TTTACCGAAT | AAAGACTGAT | CACGCCAGGT | AAGTATGGGT |
| AATGGGGAAG | AAGGAGCCTG | AATCTTACGA | TGGAATAATT | ACAAATCAGA |
| GAGGAATCAC | AATCACAGCT | CTTGGCAGAC | TGTATACCTA | TAGTCTTTGC |
| AGATCCTGTG | AAAAAAGCAT | GTGGGGCTGC | TCACTCGGGC | TGGAAGGGCA |
| CTTTGTTGGG | CGT | | | |

TABLE 17

SEQ ID NO. 16

| | | | | |
|---|---|---|---|---|
| TTTTTTTTTT | TTTTTTTTTT | TTCTTATATA | TAAATTCTAA | CCTTTAATGT |
| TTATGTAAAC | ATACATGTAT | ATGGCTATGT | AAATCTGTGG | GTATAAGTGT |
| GGATAGGTGT | TGAAACTAGA | AAGGGAACAT | AAAAGGGGAT | TGTGCAAGGG |
| AGAACAAAAC | ACATGAGACA | GGAAAGAGGG | GCTTCTGCAG | TGAAAGGGTA |
| CACAAGGGGC | CAGGGAAAGG | GAGAGCGGAG | GGCCAGAAAA | ACATGGTGCT |
| TGAGAATAGC | ATAAGGAAAC | CTGGTATTTA | TAAGGCAGTT | AAAAA |

TABLE 18

SEQ ID NO. 17

| | | | | |
|---|---|---|---|---|
| TCGGGCAGGA | AGGGCACTTT | GTTGGGCGTC | GCTATGGCTA | CTGTGAATGC |
| AGTGATAGCA | GAATATGGCT | GTAGTCTGGA | GGACATCGTT | GTTGTTCTGG |
| GCCCTTCAGT | GGGATCTTGC | TGCTTTACTC | TTCCCAGAGA | ATCAGCAACC |
| TCATTTCACA | ATGTTCATCC | TTCGTGTGTG | AGACAGTTTG | ACTCACCAAA |
| TCCCTGCGTT | GACATCCGAA | AAGCCACCAG | GATTCTTCTA | GAACGAGGAG |
| GAATTCTTCC | ACAGAATATC | AAGACCAGGA | GGAAGATCTG | ACCTCTGCAC |
| ATCTGCCATC | TGAGAG | | | |

TABLE 19

SEQ ID NO. 18

| | | | | |
|---|---|---|---|---|
| TTTTTTTTTT | TTTTTTTATA | TATAAATTCT | AACCATTTAA | TGTTTACGTA |
| AACATACATG | TATATGGCTA | TGTAAATCTG | TGGGTATAAG | TGTGGATAGG |
| AGTTGAAACT | AGAAAGGGAA | CATAAAAGGG | GATTGTGCAA | GGGAGAACAA |
| AACACATGAG | ACAGGAAAGA | GGGGCTTCTG | CAGTGAAAGG | GTACACAAGG |
| GGCCAGGGAA | AGGGAGAGCG | GAGGGCCAGA | AAAACATGGT | GCTTGAGAAC |
| AGCATAAGGA | AACCTGGTAT | TTTATAAGGC | AGTTAAAAAT | ATACATTTAA |
| AAGGAAACGT | TTATCTCCCC | | | |

TABLE 20

SEQ ID NO. 19

| | | | | |
|---|---|---|---|---|
| CCGGGGCGCC | GGCCGGCCGT | GGCGGGAACA | CCCGAACTCC | GGTGCCCGGA |
| GGCCCGGACG | CTGTGAGGCG | GGCGAGCGGG | CGGACCCGTT | CGGGCGACTC |
| TGGGGTTCGT | TCCCCGAGGC | TGCAGCTCAC | ACCCCAGCTC | GCGGCCGCCG |
| AGGAGAGCGC | GGGAAGCGCC | CCGCGTGATT | TGGCATAAAA | GTCTTTGGGG |
| GAAAAAGGTG | CCTGACTGAA | GAATGGCAGA | AGCAGTCTTG | ATAGATCTCT |
| CTGGTTTACA | ATTGAACTCT | CAGGAAAACT | GTCATCAGAT | GGTACTGAAG |
| ACGCTGGATG | GTATCAC | | | |

TABLE 21

SEQ ID NO. 20

| | | | | |
|---|---|---|---|---|
| TTTTTTTTTT | TTTTTTTTTT | ACAGTACATA | CACACAGCAT | TTTATTTAGC |
| CATAATGAAA | TTATCAAACT | TATAGGAAAA | ATTGATGGAT | CTGGAATTAT |
| TTATTATGAG | CAAAATAATC | CAGTCTCAGA | ATAAGAAACA | CCACATGTTC |
| TTTCTTATAT | ATAAATTCTA | ACCTTAATG | TTTATGTAAA | CATACAGTAT |
| ATGGCTATGT | AAATCAGTGG | GTATAAGTGT | GGATAGGTGT | TGAAACTAGA |
| AAGGGAACAT | AAAAGGGGAT | TATCGAAGGG | AGAACAAAC | ACATGAGACA |
| GGAAAGAGGG | GCAATAGTAG | TGAAAGGGAA | TATAAGGGGC | CAGGG |

TABLE 22

SEQ ID NO. 21

| | | | | |
|---|---|---|---|---|
| CCTCCGCAGC | TGGCAAATGC | TGCAGGGTTT | AATGCAGAGA | AATTTTGCCG |
| AATAAAGACT | GATCACGCCA | GGTAAGTATG | GGTAATGGGG | AAGAAGGAGC |
| CTGAATCTTA | GCATGGAATA | ATTACAAATC | AGAGAGGAAT | CACAATCACA |
| GCTCTTGGCG | CAGACTGTAT | ACCTATAGTC | TTTGCAGATC | CTGTGAAAAA |
| AGCATGTGGG | GCTGCTCACT | CGGGCTGGAA | GGGCACTTTG | TTGGGCGTCG |
| CTATGGCTAC | TGTGAATGCT | ATGATAGCAG | AATATGGCTG | TAATCTGGAG |
| GACATCATTG | TTGTTCTGGG | CCCTTCAGT | | |

TABLE 23

SEQ ID NO. 22

| | | | | |
|---|---|---|---|---|
| TTTTTTTTTT | TTTTTTTTT | TACAGTACAT | ACACACAGTA | TTTTATTTAG |
| CCATAATGAA | ATTATCAAAC | TTATAGGAAA | AATTGATGGA | TCTGGAATTA |
| TTTATTATGA | GCAAAATAAT | CCAGACTCAG | AATAAGAAAC | ACCACATGTT |

TABLE 23-continued

SEQ ID NO. 22

| | | | | |
|---|---|---|---|---|
| CTTTACTTAT | ATATAAATTC | TAACCTTTAA | TGTTTATGTA | AACATACATG |
| TATATGGCTA | TGTAAATCTG | TGGGTATAAG | TGTGGATAGG | TGTTGAAACT |
| AGAAAGGGAA | CATAAAACGG | GGATTATGCA | AGGGAGAACA | AAACACATGA |
| GACAGGAAAG | AGGGGCTTCT | G | | |

TABLE 24

SEQ ID NO. 23

| | | | | |
|---|---|---|---|---|
| CCTCCGCAGG | CTGGCAAATG | CTGCAGGGTT | TGGTGTAGAG | AAATTTTACC |
| GAATAAAGAC | TGATCATGTT | AGTGAAGTAT | GGGTAATGGG | GAAGAAGGAG |
| CCTGAATCTT | ACGATGGAAT | AATTACAAAT | CAGAGAGGAA | TCACAATCAC |
| AGCTCTTGGC | GCAGACTGTA | TACCTATAGT | CTTTGCAGAT | CCTGTGAAAA |
| AAGCATGTGG | GGCTGCTCAC | TCGGGCTGGA | AGGGCACTTT | GTTGGGCGTC |
| GCTATGGCTA | CTGTGAATGC | TATGATAGCA | | |

TABLE 25

SEQ ID NO. 24

| | | | | |
|---|---|---|---|---|
| GCAGATTTGG | CATAAAAGTC | TTTGGGGGAA | AAAGGTGCCT | GACTGAAGAA |
| TGGCAGAAGC | AGTCTTGATA | GATCTCTCTG | GTTTACAATT | GAACTCTCAG |
| GAAAACTGTC | ATCAGATGGT | ACTGAAGACG | CAGGATGGTA | TTCACGACCA |
| CCATGCCCCC | AAGGCCAAGT | TCCTTTGTAT | AATATGTTGC | AGCGATGCCA |
| CCAATGGAAA | GGGTGGGGAA | TATGGCCTCT | GTGAACTGGA | AGCAGGAAAT |
| GGCAAAACAA | GTCACGCGGA | AAATTCGAGA | CTGTTAGCCG | T |

TABLE 26

SEQ ID NO. 25

| | | | | |
|---|---|---|---|---|
| TTTTTTTTTT | TTTTTTTTAA | ACAAGGAAAC | AAAACTAGCA | CTCATCGCTT |
| TTTAGACAAT | ACATAATTAT | TCAAAATTAA | CTATTACCGG | AAGGCAAGGG |
| GGCCATACTA | ATGGGCTTG | TCTCACATGA | GTGCATGTGG | GTAGGTGCAG |
| GACGACTGAC | ATTATGCAGA | AACGAATTTT | AATTTTTAAT | CTTTAGTTTG |
| ATTTAAACAT | TGCTTTTAGT | ATGATGACAA | CACCAGCTGT | GCAGAAAGGG |
| CTCTGGAGAT | GCGTTCATAG | CAGCACACAC | CTGCGGCTCT | TCTTCGGTTC |
| TGGAGGCT | | | | |

TABLE 27

SEQ ID NO. 26

| | | | | |
|---|---|---|---|---|
| CTCACACCCC | AGCTCGCGGC | CGCCGAGGAG | AGCGCGGGAA | GCGCCCCGCG |
| TGATTTGGCA | TAAAAGTCTT | TGGGGGAAAA | AGGTGCCTGA | CTGAAGAATG |
| GCAGAAGCAG | TCTTGATAGA | TCTCTCTGGT | TTACAATTGA | ACTCTCAGGA |
| AAACTGTCAT | CAGATGGTAC | TGAAGACGCT | GGATGGTATT | CACGACCACC |
| ATGCCCCAA | GGCCAAGTTC | CTTTGTATAA | TATGTTGCAG | CGATGCCACC |
| AATGGAAAGG | GTGGGGAATA | TGGCCTCTGT | GAACTGGAAG | CAGGAATGGC |

TABLE 28

SEQ ID NO. 27

| | | | | |
|---|---|---|---|---|
| TTTTTTTTTT | TTTTTTTTTT | TTTTTTTTTT | TTTTTTTACA | GTACATACAC |
| ACAGTATTTT | ATTTAGCCAT | AATGAAATTA | TCAAACTTAT | AGGAAAAATT |
| GATGGATCTG | GAATTATTTA | TTATGAGCAA | AATAATCCAG | ACTCAGAATA |
| AGAAACACCA | CATGTTCTTT | CTTATATATA | AATTCTAACC | TTTAATGTTT |
| ATGTAAACAT | ACATGTATAT | GGCTGTGTAA | ATCTGTGGGT | ATAAGTGTGG |
| ATGGGTGTTG | AAACTAGAAA | GGGAACATAA | AAGGGGGATT | GTGCAAGGGA |

TABLE 28-continued

SEQ ID NO. 27

| GAACAAAACA | CATGAGACAG | GAAAGAGGGG | CTTCTGCGGT |
|---|---|---|---|

---

What is claimed is:

1. An isolated DNA molecule comprising a sequence encoding a polypeptide which comprises the amino acid sequence of SEQ ID NO:5.

2. The isolated DNA molecule of claim 1, wherein said molecule comprises the sequence of SEQ ID NO:4.

3. A substantially pure preparation of allograft inflammatory factor-1 polypeptide having the amino acid sequence of SEQ ID:5.

* * * * *

UNITED STATES PATENT AND TRADEMARK OFFICE
CERTIFICATE OF CORRECTION

PATENT NO. : 5,527,884

DATED : June 18, 1996

INVENTOR(S) : Mary E. Russell and Ulrike Utans

It is certified that error appears in the above-identified patent and that said Letters Patent is hereby corrected as shown below:

On the title page:

Under References Cited [56] (PUBLICATIONS):

Sharples reference, "Occulusive" should be --Occlusive--.

Steinbeck reference, "Intracellular" should be --Extracellular--.

Fyfe reference, "Activaiton" should be --Activation--.

Under References Cited [56], (OTHER PUBLICATIONS):

Liaw reference, "insert --Comparison-- before "of"; insert --Endothelium-- after "Aortic".

Signed and Sealed this

Twenty-eighth Day of April, 1998

*Attest:*

BRUCE LEHMAN

*Attesting Officer*  *Commissioner of Patents and Trademarks*

SEQUENCE LISTING ( 1 ) GENERAL INFORMATION:

( i i i ) NUMBER OF SEQUENCES: 32

( 2 ) INFORMATION FOR SEQ ID NO: 1:

( i ) SEQUENCE CHARACTERISTICS:
        ( A ) LENGTH: 331
        ( B ) TYPE: nucleic acid
        ( C ) STRANDEDNESS: double
        ( D ) TOPOLOGY: linear ( x i ) SEQUENCE DESCRIPTION: SEQ ID NO: 1:

| GCTGCTGTCA | TTAGAAGGTC | CTCGGTCCCA | CCGTGTTATA | TCCACCTCCA | ATTAGGGCAA | 60 |
| TACAGAAATA | GCTTTCTTGG | CTGGGGGACC | AGTTGGCTTC | TGGTGTTCTT | TGTTTTTCTC | 120 |
| CTCACACATC | AGAATCATTC | TCAAGATGGC | AGATCTCTTG | CCCAGCATCA | TTCTGAGAAA | 180 |
| GTCAGAGTAA | CTGAACGTCT | CCTCGGAGCC | ACTGGACACC | TCTCTAATTA | ATTTCTTCAG | 240 |
| CTCTAGATGG | GTCTTGGGAA | CCCAAGTTTC | TCCAGCATTC | GCTTCAAGGA | CATAATATCG | 300 |
| ATATCTCCAT | TGCCATTCAG | ATCAACTCAT | G | | | 331 |

( 2 ) INFORMATION FOR SEQ ID NO: 2:

( i ) SEQUENCE CHARACTERISTICS:
        ( A ) LENGTH: 129
        ( B ) TYPE: nucleic acid
        ( C ) STRANDEDNESS: double
        ( D ) TOPOLOGY: linear ( x i ) SEQUENCE DESCRIPTION: SEQ ID NO: 2:

| ACGAGAATAT | GGCTGTAATC | TGGAGGACAT | CATTGTTGTT | CTGGGCCCTT | CAGTGGGATC | 60 |
| TGCTGCTTTA | CCTTCCAGAG | AATCAGCAAC | CTCATTTACC | AAGTTCATCT | GTGTGTGAGA | 120 |
| ACGTTGACT | | | | | | 129 |

( 2 ) INFORMATION FOR SEQ ID NO: 3:

( i ) SEQUENCE CHARACTERISTICS:
        ( A ) LENGTH: 318
        ( B ) TYPE: nucleic acid
        ( C ) STRANDEDNESS: double
        ( D ) TOPOLOGY: linear ( x i ) SEQUENCE DESCRIPTION: SEQ ID NO: 3:

| TTTTTTTTTT | TTGCAGCCAT | TGTAGAAGGA | TACGGGAAGC | ATTTATCGAA | AATTCCAGAC | 60 |
| AAGAACCTCA | TTCTCTAAGG | GATATGAAGC | CTATCTGTGT | ACCGAAGTTA | AGGCCATCAC | 120 |
| GGACATGGGA | GAAAAACTTC | TCAGGATGGC | AAGATGTGCA | GAGGTCAAGA | TCTTCCTCCT | 180 |
| GGTCTTGAAT | ATCTGTGGAA | GAATTCCTCC | TGCTTCTAGA | GATCCTGTGC | TTTTCGGATG | 240 |
| TCAACGTAGG | GATTTGGTGA | GTCAAACTGT | CTCACACACG | AAGGATGAAC | ATTGTGAAAT | 300 |
| GAGGTTGCTG | ATCTCTGG | | | | | 318 |

( 2 ) INFORMATION FOR SEQ ID NO: 4:

( i ) SEQUENCE CHARACTERISTICS:
    ( A ) LENGTH: 651
    ( B ) TYPE: nucleic acid
    ( C ) STRANDEDNESS: double
    ( D ) TOPOLOGY: linear ( x i ) SEQUENCE DESCRIPTION: SEQ ID NO: 4:

```
GAGGAGCCAG CCAACACACT GCAGCCTCAT CGTCATCTCC CCACCTAAGG CCACCAGCGT    60
CTGAGGAGCT ATGAGCCAGA GCAAGGATTT GCAGGGAGGA AAAGCTTTTG CACTGCTGAA   120
AGCCCAGCAG GAAGAGAGGT TGGATGGGAT CAACAAGCAC TTCCTCGATG ATCCCAAGTA   180
CAGCAGTGAT GAGGATCTGC AGTCCAAACT GGAGGCCTTC AAGACGAAGT ACATGGAGTT   240
TGATCTGAAT GGCAATGGAG ATATCGATAT TATGTCCTTG AAGCGAATGC TGGAGAAACT   300
TGGGGTTCCC AAGACCCATC TAGAGCTGAA GAAATTAATT AGAGAGGTGT CCAGTGGCTC   360
CGAGGAGACG TTCAGTTACT CTGACTTTCT CAGAATGATG CTGGGCAAGA GATCTGCCAT   420
CTTGAGAATG ATTCTGATGT ATGAGGAGAA AAACAAAGAA CACCAGAAGC AACTGGTCC    480
CCCAGCCAAG AAAGCTATTT CTGAGTTGCC CTAATTGGAG GTGGATATAA CACGGTGGGA   540
CCGAGGACCT TCTAATGACA GCAGCATGGG AAAAGAAGAA GCAGTTGTGA GCCAGAGTCA   600
AACTAAATAA ATAATGCTCC CTAGTGCAAA AAAAAAAAAA AAAAAAAAA A             651
```

( 2 ) INFORMATION FOR SEQ ID NO: 5:

( i ) SEQUENCE CHARACTERISTICS:
        ( A ) LENGTH: 147
        ( B ) TYPE: amino acid
        ( C ) STRANDEDNESS:
        ( D ) TOPOLOGY: linear ( x i ) SEQUENCE DESCRIPTION: SEQ ID NO: 5:

```
Met Ser Gln Ser Lys Asp Leu Gln Gly Gly Lys Ala Phe Gly Leu Leu Lys
 1               5                  10                  15
Ala Gln Gln Glu Glu Arg Leu Asp Gly Ile Asn Lys His Phe Leu Asp Asp
            20                  25                  30
Pro Lys Tyr Ser Ser Asp Glu Asp Leu Gln Ser Lys Leu Glu Ala Phe Lys
35                  40                  45                  50
Thr Lys Tyr Met Glu Phe Asp Leu Asn Gly Asn Gly Asp Ile Asp Ile Met
                55                  60                  65
Ser Leu Lys Arg Met Leu Glu Lys Leu Gly Val Pro Lys Thr His Leu Glu
        70                  75                  80                  85
Leu Lys Lys Leu Ile Arg Glu Val Ser Ser Gly Ser Glu Glu Thr Phe Ser
                    90                  95                  100
Tyr Ser Asp Phe Leu Arg Met Met Leu Gly Lys Arg Ser Ala Ile Leu Arg
            105                 110                 115
Met Ile Leu Met Tyr Glu Glu Lys Asn Lys Glu His Gln Lys Pro Thr Gly
120                 125                 130                 135
Pro Pro Ala Lys Lys Ala Ile Ser Glu Leu Pro
                140                 145
```

( 2 ) INFORMATION FOR SEQ ID NO: 6:

( i ) SEQUENCE CHARACTERISTICS:
        ( A ) LENGTH: 18
        ( B ) TYPE: nucleic acid
        ( C ) STRANDEDNESS: single
        ( D ) TOPOLOGY: linear ( x i ) SEQUENCE DESCRIPTION: SEQ ID NO: 6:

CACATCTTGC CATCCTGA                                                                                              18

(2) INFORMATION FOR SEQ ID NO: 7:

(i) SEQUENCE CHARACTERISTICS:
        (A) LENGTH: 18
        (B) TYPE: nucleic acid
        (C) STRANDEDNESS: single
        (D) TOPOLOGY: linear (xi) SEQUENCE DESCRIPTION: SEQ ID NO: 7:

CATGGTGCTT GAGAACAG                                                                                              18

(2) INFORMATION FOR SEQ ID NO: 8:

(i) SEQUENCE CHARACTERISTICS:
        (A) LENGTH: 310
        (B) TYPE: nucleic acid
        (C) STRANDEDNESS: double
        (D) TOPOLOGY: linear (xi) SEQUENCE DESCRIPTION: SEQ ID NO: 8:

GTTTAATGCA GAGAAATTTT ACCGAATAAA GACTGATCAC GCCAGGTAAG TATGGGTAAT      60
GGGGAAGAAG GAGCCTGAAT CTTACGATGG AATAATTACA AATCAGAGAG GAATCACAAT     120
CACAGCTCTT GGCGCAGACT GTATACCTAT AGTCTTTGCA GATCCTGTGA AAAAAGCATG     180
TGGGGCTGCT CACTCGGGCT GGAAGGGCAC TTTGTTGGGC GTCGCTATGG CTACTGTGAA     240
TGCTATGATA GCAGAATATG GCTGTAATCT GGAGGACATC ATTGTTGTTC TGGGCCCTTC     300
AGTGGGATCT                                                           310

(2) INFORMATION FOR SEQ ID NO: 9:

(i) SEQUENCE CHARACTERISTICS:
        (A) LENGTH: 274
        (B) TYPE: nucleic acid
        (C) STRANDEDNESS: double
        (D) TOPOLOGY: linear (xi) SEQUENCE DESCRIPTION: SEQ ID NO: 9:

TTTTTTTTC TTATATATAA ATTCTAACCT TTAATGTTTA TGTAAACATA CATGTATATG       60
GCTATGTAAA TCTGTGGGTA TAAGTGTGGA TAGGTGTTGA AACTAGAAAG GGAACATAAA     120
AGGGGATTGT GCAAGGGAGA ACAAAACACA TGAGACAGGA AAGAGGGGCT TCTGCAGTGA     180
AAGGGTACAC AAGGGGCCAG GGAAAGGGAG AGCGAGGGCC AGAAAAACAT GGTGCTTGAG     240
AACAGCATAA GGAACCTGTA TTTATAAGGC AGTT                                 274

(2) INFORMATION FOR SEQ ID NO: 10:

(i) SEQUENCE CHARACTERISTICS:
        (A) LENGTH: 388
        (B) TYPE: nucleic acid
        (C) STRANDEDNESS: double
        (D) TOPOLOGY: linear (xi) SEQUENCE DESCRIPTION: SEQ ID NO: 10:

CCGAGTCTCG CGTCTACCAG AGCTGCAAGA TGTCTGTGCT CCCTGGAATA ATTGTCCTTG      60
TGGACGATC CTCATGTGCC TGGTGTGCCT GCTTGCTAGT AGGAGGAATA ATACCGGTTC      120
ATTCTCCTAC CGGAACACCA ATATGTATAT GTGCATCGGC CCCAAGTCAT CATTGAAAAC     180
ACAGTGTTCT CAAGTGGACA AGACCTTCAC TGGATTGTTC AAGAGAGATC CAGCCTTACA     240
AGAAGGAAAA CTAGAGACCA AAATAAATCC TCTTCCTTCT CGATGGGTAT CATCTGCTTC     300

| TTCTTCCTAA | AAGACTGGGG | GAGCTATCTC | TCATAGTGAG | TACATTCAGT | GTGCAAGTGG | 360 |
| CTCTCAGAGT | AGACTCAGTC | CTTGCTTG | | | | 388 |

(2) INFORMATION FOR SEQ ID NO: 11:

(i) SEQUENCE CHARACTERISTICS:
        (A) LENGTH: 309
        (B) TYPE: nucleic acid
        (C) STRANDEDNESS: double
        (D) TOPOLOGY: linear (xi) SEQUENCE DESCRIPTION: SEQ ID NO: 11:

| TCGAGTTTTT | TTTTTTTTT | TTTATATATA | AATTCTAACC | TTTAATGTTT | ATGTAAACAT | 60 |
| ACATGTATAT | GGCAATGTAA | ATCTGTGGGT | ATAAGTGTGG | ATAGGTGTTG | AAACTAGAAA | 120 |
| GGGAACATAA | AAGGGGATTG | TGCAAGGGAG | AACAAAACAC | ATGACAGGAA | AGAGGGGCTT | 180 |
| CTGCAGTGAA | AGGGTACACA | AGGGGCCAGG | GAAAGGGAGA | GCGGAGGGCC | AGAAAAACAT | 240 |
| GGTGCTTGAG | AACAGCATAA | GGAAACCTGT | ATTTTATAAG | GCAGTTAAAA | TATACATTTA | 300 |
| AAAGGAACG | | | | | | 309 |

(2) INFORMATION FOR SEQ ID NO: 12:

(i) SEQUENCE CHARACTERISTICS:
        (A) LENGTH: 362
        (B) TYPE: nucleic acid
        (C) STRANDEDNESS: double
        (D) TOPOLOGY: linear (xi) SEQUENCE DESCRIPTION: SEQ ID NO: 12:

| TTTTTTTTTT | TTTTTTTTT | TTTTTTTTT | CTTATATATA | AATTCTAACC | TTTAATGTTT | 60 |
| ATGTAAACAT | ACATGTATAT | GGCTATGTAA | ATCTGTGGGT | ATAAGTGTGG | ATAGGTGTTG | 120 |
| AAACTAGAAA | GGGAACATAA | AAGGGGATTG | TGCAAGGGAG | AACAAAACAC | ATGAGACAGG | 180 |
| AAAGAGGGGC | TTCTGCAGTG | AAAGGGTACA | CAAGGGGCCA | GGGAAAGGGA | GACGGAGGGC | 240 |
| CAGAAAAACA | TGGTGCTTGA | GAACAGCATA | AGGAAACCTG | GTATTTTATA | AGGCAGTTAA | 300 |
| AAATATACAT | TTAAAAGGAA | ACGTTTATCT | CCCCTACTGC | ATTTGATTCA | AATGAGAAGG | 360 |
| TG | | | | | | 362 |

(2) INFORMATION FOR SEQ ID NO: 13:

(i) SEQUENCE CHARACTERISTICS:
        (A) LENGTH: 347
        (B) TYPE: nucleic acid
        (C) STRANDEDNESS: double
        (D) TOPOLOGY: linear (xi) SEQUENCE DESCRIPTION: SEQ ID NO: 13:

| GAAAAGGTG | CCTGACTGAA | GAATGGCAGA | AGCAGTCTTG | ATAGATCTCT | CTGGTTTACA | 60 |
| ATTGAACTCT | CAGGAAAACT | GTCATCAGAT | GGTACTGAAG | ACGCTGGATG | GTATTCACGA | 120 |
| CCACCATGCC | CCCAAGGCCA | AGTTCCTTTG | TATAATATGT | TGCAGCGATG | CCACCAATGG | 180 |
| AAAGGGTGGG | GAATATGGCC | TCTGTGAACT | GGAAGCAGGA | AATGGCTTTT | CAAGTCTCGC | 240 |
| GGGAAAATTC | GAGACTGTTA | GCCATCCAGC | CTGGCTGCCT | CTTTGTATTC | AGTTAAACAA | 300 |
| AAATAGATGA | GGAGGATCTG | AGCCGCGTTA | AGGTGATTGT | GCCCGAG | | 347 |

(2) INFORMATION FOR SEQ ID NO: 14:

(i) SEQUENCE CHARACTERISTICS:
        (A) LENGTH: 350

( B ) TYPE: nucleic acid
( C ) STRANDEDNESS: double
( D ) TOPOLOGY: linear ( x i ) SEQUENCE DESCRIPTION: SEQ ID NO: 14:

```
TTTTTTTTT  TTTTTTTTT  TTTTTTTTT  TTTTTTTTT  ACATACACAC  AGTATTTTAT   60
TTAGCCATAA  TGAAATTATC  AAACTTATAG  GAAAAATTGA  TGGATCTGGA  ATTATTTTAT  120
ATGAGCAAAA  TAATCCAGAC  TCAGAATAAG  AAACACCACA  TGTTCTTTCT  TATATATAAA  180
TTCTAACCTT  TAATGTTTAT  GTAAACATAC  ATGTATATGG  CTATGTAAAT  CTGTGGGTAT  240
AAGTGTGGAT  AGGTGTTGAA  ACTAGAAAGG  GAACATAAAA  GGGGATTGTG  CAAGGGAGAA  300
CAAAACATAT  GAGACAGGAA  AGAGGGGCTT  CTGTAGTGAA  AGGGTACCAA              350
```

( 2 ) INFORMATION FOR SEQ ID NO: 15:

( i ) SEQUENCE CHARACTERISTICS:
( A ) LENGTH: 313
( B ) TYPE: nucleic acid
( C ) STRANDEDNESS: double
( D ) TOPOLOGY: linear ( x i ) SEQUENCE DESCRIPTION: SEQ ID NO: 15:

```
TCTCAGCTCA  CTCAATCTTT  TCAGTAGTTC  CAAACGGAGA  GATCCCAAAG  TGGTTGTTCA   60
AGAAAACCTC  CGCGGCCTGG  CAAATGCTGC  AGGGTTTAAT  GCAGAGAAAT  TTTACCGAAT  120
AAAGACTGAT  CACGCCAGGT  AAGTATGGGT  AATGGGGAAG  AAGGAGCCTG  AATCTTACGA  180
TGGAATAATT  ACAAATCAGA  GAGGAATCAC  AATCACAGCT  CTTGGCAGAC  TGTATACCTA  240
TAGTCTTTGC  AGATCCTGTG  AAAAAAGCAT  GTGGGGCTGC  TCACTCGGGC  TGGAAGGGCA  300
CTTTGTTGGG  CGT                                                         313
```

( 2 ) INFORMATION FOR SEQ ID NO: 16:

( i ) SEQUENCE CHARACTERISTICS:
( A ) LENGTH: 295
( B ) TYPE: nucleic acid
( C ) STRANDEDNESS: double
( D ) TOPOLOGY: linear ( x i ) SEQUENCE DESCRIPTION: SEQ ID NO: 16:

```
TTTTTTTTT  TTTTTTTTT  TTCTTATATA  TAAATTCTAA  CCTTTAATGT  TTATGTAAAC   60
ATACATGTAT  ATGGCTATGT  AAATCTGTGG  GTATAAGTGT  GGATAGGTGT  TGAAACTAGA  120
AAGGGAACAT  AAAAGGGGAT  TGTGCAAGGG  AGAACAAAAC  ACATGAGACA  GGAAAGAGGG  180
GCTTCTGCAG  TGAAAGGGTA  CACAAGGGGC  CAGGGAAAGG  GAGAGCGGAG  GGCCAGAAAA  240
ACATGGTGCT  TGAGAATAGC  ATAAGGAAAC  CTGGTATTTA  TAAGGCAGTT  AAAAA       295
```

( 2 ) INFORMATION FOR SEQ ID NO: 17:

( i ) SEQUENCE CHARACTERISTICS:
( A ) LENGTH: 316
( B ) TYPE: nucleic acid
( C ) STRANDEDNESS: double
( D ) TOPOLOGY: linear ( x i ) SEQUENCE DESCRIPTION: SEQ ID NO: 17:

```
TCGGGCAGGA  AGGGCACTTT  GTTGGGCGTC  GCTATGGCTA  CTGTGAATGC  AGTGATAGCA   60
GAATATGGCT  GTAGTCTGGA  GGACATCGTT  GTTGTTCTGG  GCCCTTCAGT  GGGATCTTGC  120
TGCTTTACTC  TTCCCAGAGA  ATCAGCAACC  TCATTTCACA  ATGTTCATCC  TTCGTGTGTG  180
AGACAGTTTG  ACTCACCAAA  TCCCTGCGTT  GACATCCGAA  AAGCCACCAG  GATTCTTCTA  240
```

```
GAACGAGGAG  GAATTCTTCC  ACAGAATATC  AAGACCAGGA  GGAAGATCTG  ACCTCTGCAC      300

ATCTGCCATC  TGAGAG                                                         316
```

( 2 ) INFORMATION FOR SEQ ID NO: 18:

( i ) SEQUENCE CHARACTERISTICS:
    ( A ) LENGTH: 320
    ( B ) TYPE: nucleic acid
    ( C ) STRANDEDNESS: double
    ( D ) TOPOLOGY: linear ( x i ) SEQUENCE DESCRIPTION: SEQ ID NO: 18:

```
TTTTTTTTTT  TTTTTTTATA  TATAAATTCT  AACCATTTAA  TGTTTACGTA  AACATACATG      60

TATATGGCTA  TGTAAATCTG  TGGGTATAAG  TGTGGATAGG  AGTTGAAACT  AGAAAGGGAA     120

CATAAAAGGG  GATTGTGCAA  GGGAGAACAA  AACACATGAG  ACAGGAAAGA  GGGGCTTCTG     180

CAGTGAAAGG  GTACACAAGG  GGCCAGGGAA  AGGGAGAGCG  GAGGGCCAGA  AAAACATGGT     240

GCTTGAGAAC  AGCATAAGGA  AACCTGGTAT  TTTATAAGGC  AGTTAAAAAT  ATACATTTAA     300

AAGGAAACGT  TTATCTCCCC                                                    320
```

( 2 ) INFORMATION FOR SEQ ID NO: 19:

( i ) SEQUENCE CHARACTERISTICS:
    ( A ) LENGTH: 317
    ( B ) TYPE: nucleic acid
    ( C ) STRANDEDNESS: double
    ( D ) TOPOLOGY: linear ( x i ) SEQUENCE DESCRIPTION: SEQ ID NO: 19:

```
CCGGGGCGCC  GGCCGGCCGT  GGCGGGAACA  CCCGAACTCC  GGTGCCCGGA  GGCCCGGACG      60

CTGTGAGGCG  GGCGAGCGGG  CGGACCCGTT  CGGGCGACTC  TGGGGTTCGT  TCCCCGAGGC     120

TGCAGCTCAC  ACCCCAGCTC  GCGGCCGCCG  AGGAGAGCGC  GGGAAGCGCC  CCGCGTGATT     180

TGGCATAAAA  GTCTTTGGGG  GAAAAAGGTG  CCTGACTGAA  GAATGGCAGA  AGCAGTCTTG     240

ATAGATCTCT  CTGGTTTACA  ATTGAACTCT  CAGGAAAACT  GTCATCAGAT  GGTACTGAAG     300

ACGCTGGATG  GTATCAC                                                       317
```

( 2 ) INFORMATION FOR SEQ ID NO: 20:

( i ) SEQUENCE CHARACTERISTICS:
    ( A ) LENGTH: 345
    ( B ) TYPE: nucleic acid
    ( C ) STRANDEDNESS: double
    ( D ) TOPOLOGY: linear ( x i ) SEQUENCE DESCRIPTION: SEQ ID NO: 20:

```
TTTTTTTTTT  TTTTTTTTTT  ACAGTACATA  CACACAGCAT  TTTATTTAGC  CATAATGAAA      60

TTATCAAACT  TATAGGAAAA  ATTGATGGAT  CTGGAATTAT  TTATTATGAG  CAAAATAATC     120

CAGTCTCAGA  ATAAGAAACA  CCACATGTTC  TTTCTTATAT  ATAAATTCTA  ACCTTTAATG     180

TTTATGTAAA  CATACAGTAT  ATGGCTATGT  AAATCAGTGG  GTATAAGTGT  GGATAGGTGT     240

TGAAACTAGA  AAGGGAACAT  AAAAGGGGAT  TATCGAAGGG  AGAACAAAAC  ACATGAGACA     300

GGAAAGAGGG  GCAATAGTAG  TGAAAGGGAA  TATAAGGGGC  CAGGG                     345
```

( 2 ) INFORMATION FOR SEQ ID NO: 21:

( i ) SEQUENCE CHARACTERISTICS:
    ( A ) LENGTH: 329
    ( B ) TYPE: nucleic acid ( C ) STRANDEDNESS: double
( D ) TOPOLOGY: linear ( x i ) SEQUENCE DESCRIPTION: SEQ ID NO: 21:

| | | | | | | |
|---|---|---|---|---|---|---|
| CCTCCGCAGC | TGGCAAATGC | TGCAGGGTTT | AATGCAGAGA | AATTTTGCCG | AATAAAGACT | 60 |
| GATCACGCCA | GGTAAGTATG | GGTAATGGGG | AAGAAGGAGC | CTGAATCTTA | GCATGGAATA | 120 |
| ATTACAAATC | AGAGAGGAAT | CACAATCACA | GCTCTTGGCG | CAGACTGTAT | ACCTATAGTC | 180 |
| TTTGCAGATC | CTGTGAAAAA | AGCATGTGGG | GCTGCTCACT | CGGGCTGGAA | GGGCACTTTG | 240 |
| TTGGGCGTCG | CTATGGCTAC | TGTGAATGCT | ATGATAGCAG | AATATGGCTG | TAATCTGGAG | 300 |
| GACATCATTG | TTGTTCTGGG | CCCTTCAGT | | | | 329 |

( 2 ) INFORMATION FOR SEQ ID NO: 22:

( i ) SEQUENCE CHARACTERISTICS:
        ( A ) LENGTH: 321
        ( B ) TYPE: nucleic acid
        ( C ) STRANDEDNESS: double
        ( D ) TOPOLOGY: linear ( x i ) SEQUENCE DESCRIPTION: SEQ ID NO: 22:

| | | | | | | |
|---|---|---|---|---|---|---|
| TTTTTTTTTT | TTTTTTTTTT | TACAGTACAT | ACACACAGTA | TTTTATTTAG | CCATAATGAA | 60 |
| ATTATCAAAC | TTATAGGAAA | AATTGATGGA | TCTGGAATTA | TTTATTATGA | GCAAAATAAT | 120 |
| CCAGACTCAG | AATAAGAAAC | ACCACATGTT | CTTTACTTAT | ATATAAATTC | TAACCTTTAA | 180 |
| TGTTTATGTA | AACATACATG | TATATGGCTA | TGTAAATCTG | TGGGTATAAG | TGTGGATAGG | 240 |
| TGTTGAAACT | AGAAAGGGAA | CATAAAACGG | GGATTATGCA | AGGGAGAACA | AAACACATGA | 300 |
| GACAGGAAAG | AGGGGCTTCT | G | | | | 321 |

( 2 ) INFORMATION FOR SEQ ID NO: 23:

( i ) SEQUENCE CHARACTERISTICS:
        ( A ) LENGTH: 280
        ( B ) TYPE: nucleic acid
        ( C ) STRANDEDNESS: double
        ( D ) TOPOLOGY: linear ( x i ) SEQUENCE DESCRIPTION: SEQ ID NO: 23:

| | | | | | | |
|---|---|---|---|---|---|---|
| CCTCCGCAGG | CTGGCAAATG | CTGCAGGGTT | TGGTGTAGAG | AAATTTTACC | GAATAAAGAC | 60 |
| TGATCATGTT | AGTGAAGTAT | GGGTAATGGG | GAAGAAGGAG | CCTGAATCTT | ACGATGGAAT | 120 |
| AATTACAAAT | CAGAGAGGAA | TCACAATCAC | AGCTCTTGGC | GCAGACTGTA | TACCTATAGT | 180 |
| CTTTGCAGAT | CCTGTGAAAA | AAGCATGTGG | GGCTGCTCAC | TCGGGCTGGA | AGGGCACTTT | 240 |
| GTTGGGCGTC | GCTATGGCTA | CTGTGAATGC | TATGATAGCA | | | 280 |

( 2 ) INFORMATION FOR SEQ ID NO: 24:

( i ) SEQUENCE CHARACTERISTICS:
        ( A ) LENGTH: 291
        ( B ) TYPE: nucleic acid
        ( C ) STRANDEDNESS: double
        ( D ) TOPOLOGY: linear ( x i ) SEQUENCE DESCRIPTION: SEQ ID NO: 24:

| | | | | | | |
|---|---|---|---|---|---|---|
| GCAGATTTGG | CATAAAAGTC | TTTGGGGGAA | AAAGGTGCCT | GACTGAAGAA | TGGCAGAAGC | 60 |
| AGTCTTGATA | GATCTCTCTG | GTTACAATT | GAACTCTCAG | GAAAACTGTC | ATCAGATGGT | 120 |
| ACTGAAGACG | CAGGATGGTA | TTCACGACCA | CCATGCCCCC | AAGGCCAAGT | TCCTTTGTAT | 180 |
| AATATGTTGC | AGCGATGCCA | CCAATGGAAA | GGGTGGGGAA | TATGGCCTCT | GTGAACTGGA | 240 |

AGCAGGAAAT GGCAAAACAA GTCACGCGGA AAATTCGAGA CTGTTAGCCG T          291

( 2 ) INFORMATION FOR SEQ ID NO: 25:

( i ) SEQUENCE CHARACTERISTICS:
        ( A ) LENGTH: 308
        ( B ) TYPE: nucleic acid
        ( C ) STRANDEDNESS: double
        ( D ) TOPOLOGY: linear ( x i ) SEQUENCE DESCRIPTION: SEQ ID NO: 25:

TTTTTTTTTT TTTTTTTTAA ACAAGGAAAC AAAACTAGCA CTCATCGCTT TTTAGACAAT    60

ACATAATTAT TCAAAATTAA CTATTACCGG AAGGCAAGGG GGCCATACTA ATGGGCCTTG   120

TCTCACATGA GTGCATGTGG GTAGGTGCAG GACGACTGAC ATTATGCAGA AACGAATTTT   180

AATTTTTAAT CTTTAGTTTG ATTTAAACAT TGCTTTTAGT ATGATGACAA CACCAGCTGT   240

GCAGAAAGGG CTCTGGAGAT GCGTTCATAG CAGCACACAC CTGCGGCTCT TCTTCGGTTC   300

TGGAGGCT                                                           308

( 2 ) INFORMATION FOR SEQ ID NO: 26:

( i ) SEQUENCE CHARACTERISTICS:
        ( A ) LENGTH: 300
        ( B ) TYPE: nucleic acid
        ( C ) STRANDEDNESS: double
        ( D ) TOPOLOGY: linear ( x i ) SEQUENCE DESCRIPTION: SEQ ID NO: 26:

CTCACACCCC AGCTCGCGGC CGCCGAGGAG AGCGCGGGAA GCGCCCCGCG TGATTTGGCA    60

TAAAAGTCTT TGGGGGAAAA AGGTGCCTGA CTGAAGAATG GCAGAAGCAG TCTTGATAGA   120

TCTCTCTGGT TTACAATTGA ACTCTCAGGA AAACTGTCAT CAGATGGTAC TGAAGACGCT   180

GGATGGTATT CACGACCACC ATGCCCCAA GGCCAAGTTC CTTTGTATAA TATGTTGCAG    240

CGATGCCACC AATGGAAAGG GTGGGGAATA TGGCCTCTGT GAACTGGAAG CAGGAATGGC   300

( 2 ) INFORMATION FOR SEQ ID NO: 27:

( i ) SEQUENCE CHARACTERISTICS:
        ( A ) LENGTH: 340
        ( B ) TYPE: nucleic acid
        ( C ) STRANDEDNESS: double
        ( D ) TOPOLOGY: linear ( x i ) SEQUENCE DESCRIPTION: SEQ ID NO: 27:

TTTTTTTTTT TTTTTTTTTT TTTTTTTTTT TTTTTTACA GTACATACAC ACAGTATTTT    60

ATTTAGCCAT AATGAAATTA TCAAACTTAT AGGAAAAATT GATGGATCTG GAATTATTA   120

TTATGAGCAA AATAATCCAG ACTCAGAATA AGAAACACCA CATGTTCTTT CTTATATATA   180

AATTCTAACC TTTAATGTTT ATGTAAACAT ACATGTATAT GGCTGTGTAA ATCTGTGGGT   240

ATAAGTGTGG ATGGGTGTTG AAACTAGAAA GGGAACATAA AAGGGGATT GTGCAAGGA    300

GAACAAAACA CATGAGACAG GAAAGAGGGG CTTCTGCGGT                        340

( 2 ) INFORMATION FOR SEQ ID NO: 28:

( i ) SEQUENCE CHARACTERISTICS:
        ( A ) LENGTH: 10
        ( B ) TYPE: nucleic acid
        ( C ) STRANDEDNESS: single
        ( D ) TOPOLOGY: linear ( x i ) SEQUENCE DESCRIPTION: SEQ ID NO: 28:

```
AGCCAGCGAA                                                                                              10
```

(2) INFORMATION FOR SEQ ID NO: 29:

(i) SEQUENCE CHARACTERISTICS:
    (A) LENGTH: 10
    (B) TYPE: nucleic acid
    (C) STRANDEDNESS: single
    (D) TOPOLOGY: linear (xi) SEQUENCE DESCRIPTION: SEQ ID NO: 29:

```
AATCGGGCTG                                                                                              10
```

(2) INFORMATION FOR SEQ ID NO: 30:

(i) SEQUENCE CHARACTERISTICS:
    (A) LENGTH: 10
    (B) TYPE: nucleic acid
    (C) STRANDEDNESS: single
    (D) TOPOLOGY: linear (xi) SEQUENCE DESCRIPTION: SEQ ID NO: 30:

```
TCTGTGCTGG                                                                                              10
```

(2) INFORMATION FOR SEQ ID NO: 31:

(i) SEQUENCE CHARACTERISTICS:
    (A) LENGTH: 18
    (B) TYPE: nucleic acid
    (C) STRANDEDNESS: single
    (D) TOPOLOGY: linear (xi) SEQUENCE DESCRIPTION: SEQ ID NO: 31:

```
CCTAGAAACC  CTGAGAAC                                                                                    18
```

(2) INFORMATION FOR SEQ ID NO: 32:

(i) SEQUENCE CHARACTERISTICS:
    (A) LENGTH: 18
    (B) TYPE: nucleic acid
    (C) STRANDEDNESS: single
    (D) TOPOLOGY: linear (xi) SEQUENCE DESCRIPTION: SEQ ID NO: 32:

```
GAGTGCCGCT  TATTGTAG                                                                                    18
```